(12) United States Patent
Deckman et al.

(10) Patent No.: US 11,771,842 B2
(45) Date of Patent: Oct. 3, 2023

(54) SYRINGES, SYRINGE CONTAINERS, KITS AND METHODS OF USE

(71) Applicant: MEDICINES360, San Francisco, CA (US)

(72) Inventors: Rob Deckman, San Bruno, CA (US); Dominic Peralta, San Mateo, CA (US); Juan Ernesto, Woodside, CA (US); Kate Stephenson, Belmont, CA (US); Chinmay Deodhar, Pune (IN)

(73) Assignee: MEDICINES360, San Francisco, CA (US)

( * ) Notice: Subject to any disclaimer, the term of this patent is extended or adjusted under 35 U.S.C. 154(b) by 233 days.

(21) Appl. No.: 16/842,704

(22) Filed: Apr. 7, 2020

(65) Prior Publication Data

US 2020/0353177 A1 Nov. 12, 2020

Related U.S. Application Data

(60) Provisional application No. 62/884,429, filed on Aug. 8, 2019, provisional application No. 62/845,475, filed on May 9, 2019.

(51) Int. Cl.
*A61M 5/32* (2006.01)
*A61M 5/31* (2006.01)
*A61M 5/46* (2006.01)

(52) U.S. Cl.
CPC ............ *A61M 5/3202* (2013.01); *A61M 5/46* (2013.01); *A61M 2005/312* (2013.01); *A61M 2005/3254* (2013.01); *A61M 2202/30* (2013.01); *A61M 2205/3368* (2013.01); *A61M 2205/3592* (2013.01); *A61M 2205/52* (2013.01); *A61M 2205/584* (2013.01); *A61M 2205/587* (2013.01)

(58) Field of Classification Search
CPC .... A61M 5/282; A61M 5/288; A61M 5/2425; A61M 5/3202
See application file for complete search history.

(56) References Cited

U.S. PATENT DOCUMENTS

| | | | |
|---|---|---|---|
| 1,373,669 A | 4/1921 | Pittenger | |
| 1,522,198 A | 1/1925 | Marcy | |
| 1,668,588 A | 5/1928 | Greeley | |
| 2,771,879 A | 11/1956 | Salisbury | |
| 2,841,143 A | 7/1958 | Heinrich | |
| 2,876,771 A | 3/1959 | Paul | |
| 2,907,326 A | 10/1959 | William | |
| 3,084,793 A * | 4/1963 | Pitman | A61M 5/00 206/459.1 |

(Continued)

FOREIGN PATENT DOCUMENTS

| | | |
|---|---|---|
| DE | 1083506 B | 6/1960 |
| EP | 1680160 B1 | 7/2013 |

(Continued)

*Primary Examiner* — Laura A Bouchelle
(74) *Attorney, Agent, or Firm* — BUCHALTER; Cecily Anne O'Regan

(57) ABSTRACT

An injection devices and methods of use are disclosed. The injection devices can be single use disposable injection devices. The injection devices can be pre-loaded with a medicament or be configured to receive a fluid delivery assembly within an aperture. The injection devices are also configurable to communicate with an electronic device and/or a central location.

21 Claims, 22 Drawing Sheets

(56) References Cited

U.S. PATENT DOCUMENTS

| | | |
|---|---|---|
| 3,989,045 A | 11/1976 | Eck |
| 4,410,323 A | 10/1983 | Hodosh et al. |
| 4,548,601 A | 10/1985 | Lary |
| 4,883,473 A | 11/1989 | Thomas |
| 5,261,881 A | 11/1993 | Riner |
| 5,538,506 A | 7/1996 | Farris et al. |
| 5,549,568 A * | 8/1996 | Shields ............... A61M 5/326 |
| | | 604/263 |
| 5,713,874 A | 2/1998 | Ferber |
| 6,120,478 A | 9/2000 | Moore et al. |
| 6,656,147 B1 | 12/2003 | Gertsek et al. |
| 6,986,760 B2 * | 1/2006 | Giambattista ......... A61M 5/326 |
| | | 604/110 |
| 7,115,108 B2 | 10/2006 | Wilkinson et al. |
| 8,377,029 B2 | 2/2013 | Nagao et al. |
| 8,388,639 B2 | 3/2013 | Nicholls et al. |
| 8,926,976 B2 * | 1/2015 | Corbin ..................... A61P 3/04 |
| | | 424/143.1 |
| 9,265,889 B2 | 2/2016 | Thornton et al. |
| 9,550,025 B2 | 1/2017 | Dunne |
| 2004/0193110 A1 * | 9/2004 | Giambattista ....... A61M 5/3202 |
| | | 604/110 |
| 2005/0171477 A1 * | 8/2005 | Rubin .................... A61M 5/326 |
| | | 604/156 |
| 2010/0179473 A1 | 7/2010 | Genosar |
| 2011/0319834 A1 | 12/2011 | Modi |
| 2012/0238962 A1 | 9/2012 | Chin et al. |
| 2015/0051578 A1 | 2/2015 | Herr |
| 2018/0085527 A1 | 3/2018 | Taylor et al. |

FOREIGN PATENT DOCUMENTS

| | | | |
|---|---|---|---|
| EP | 3381493 A1 | 10/2018 | |
| EP | 3965853 A1 | 3/2022 | |
| GB | 2258618 A * | 2/1993 | ........... A61B 17/205 |
| WO | WO 89/10765 A2 * | 11/1989 | |
| WO | WO-8910765 A2 * | 11/1989 | ........ A61M 5/31525 |
| WO | 2005002649 A1 | 1/2005 | |
| WO | WO-2015136564 A1 * | 9/2015 | ........ A61M 5/31525 |
| WO | 2018136840 A1 | 7/2018 | |
| WO | 2020226923 A1 | 11/2020 | |

* cited by examiner

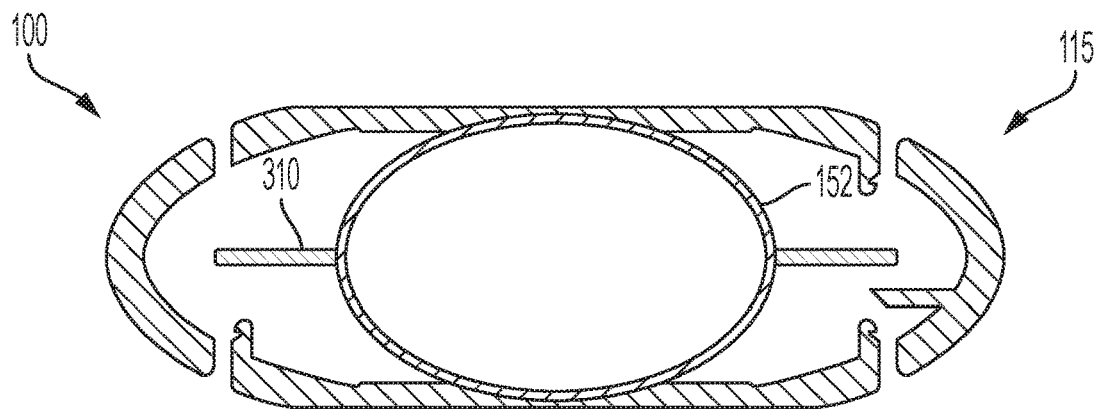
FIG. 3E
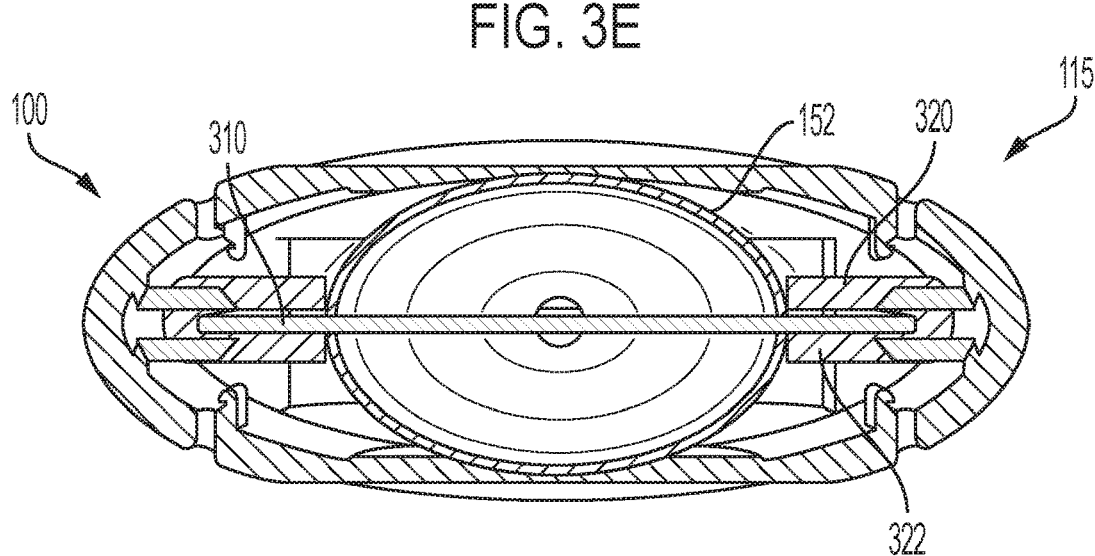
FIG. 3F
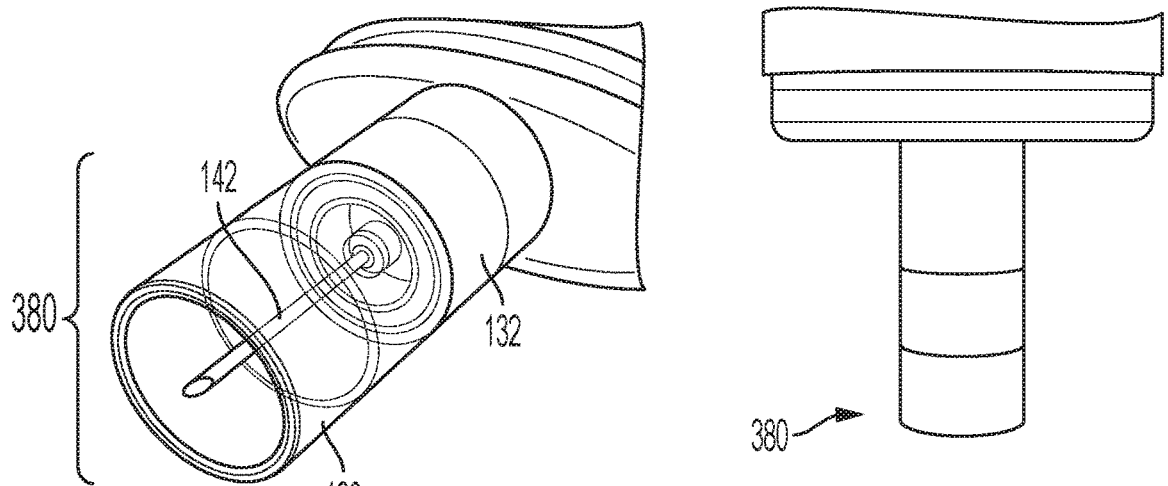
FIG. 3G
FIG. 3H

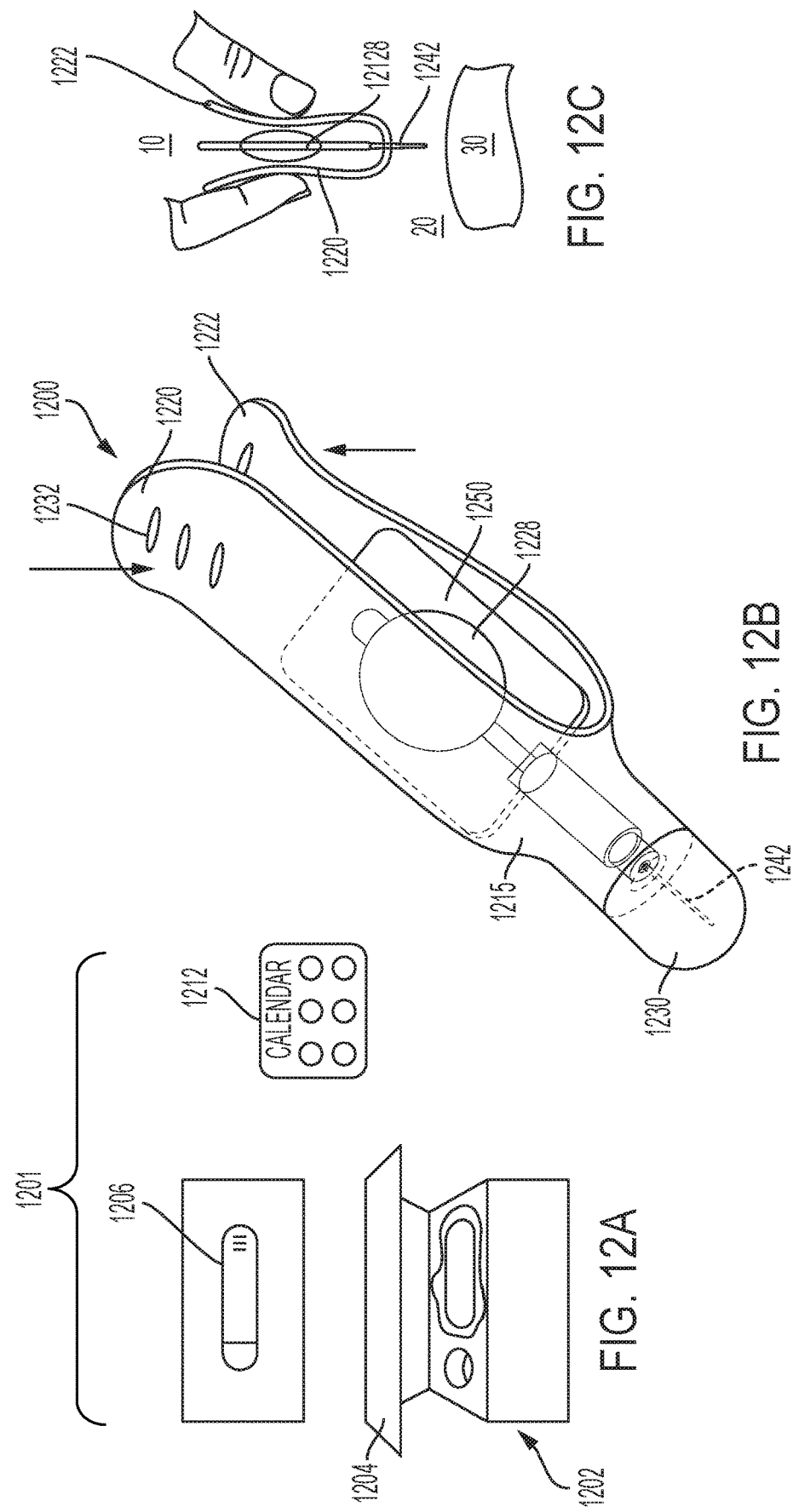

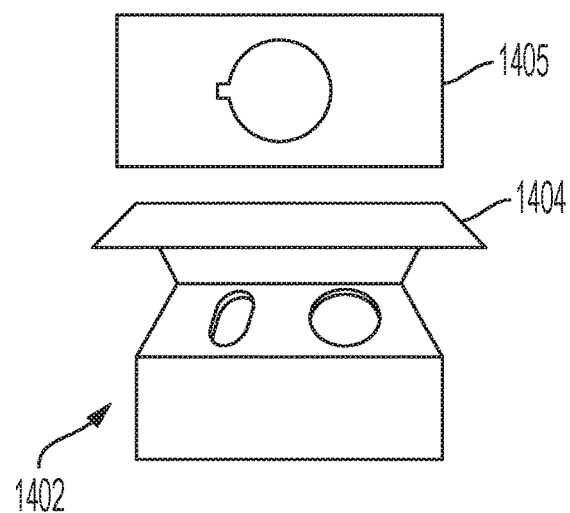
FIG. 14A
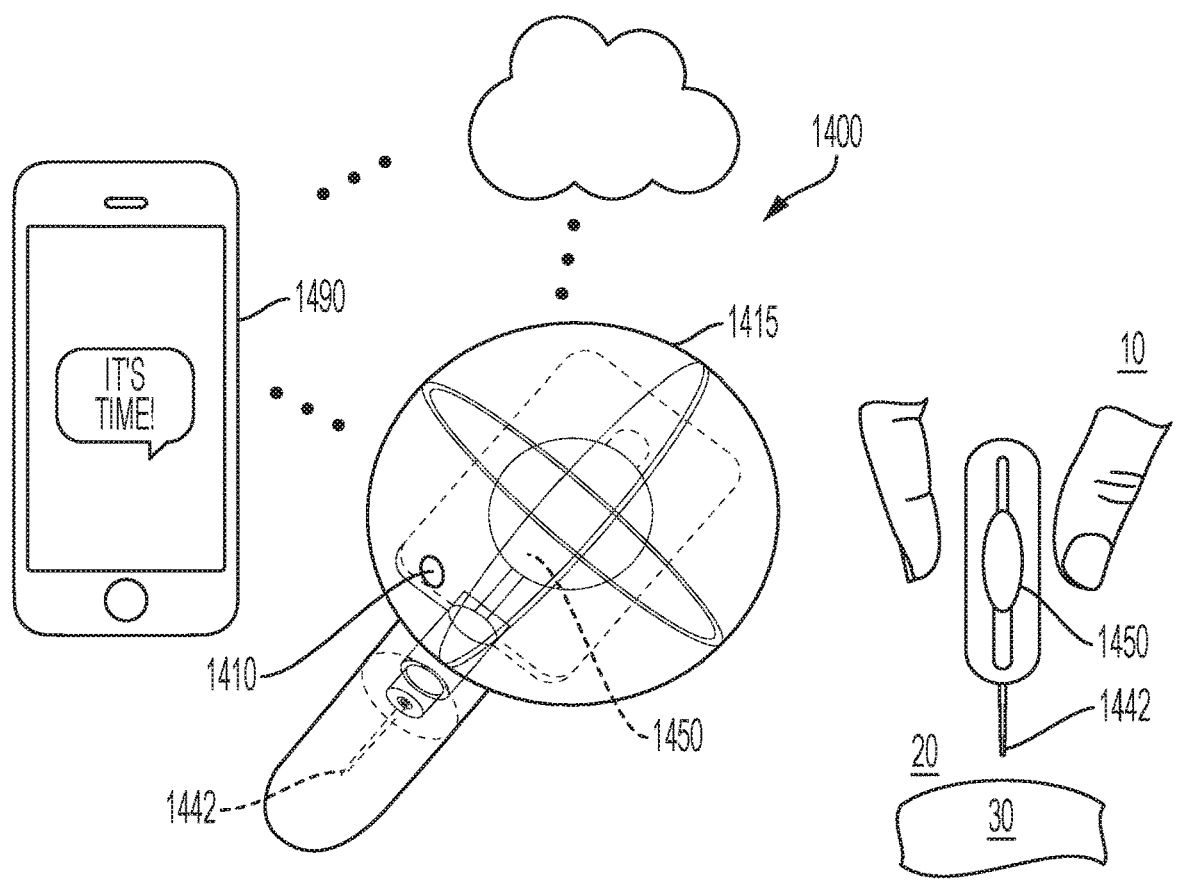
FIG. 14B
FIG. 14C

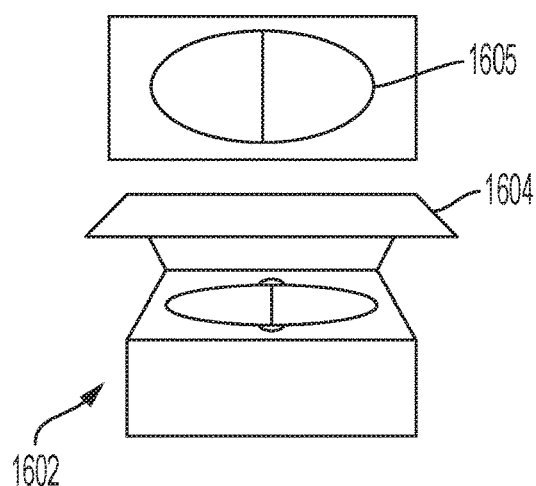
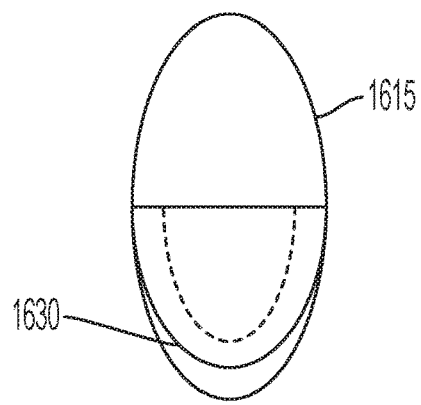
FIG. 16A
FIG. 16B
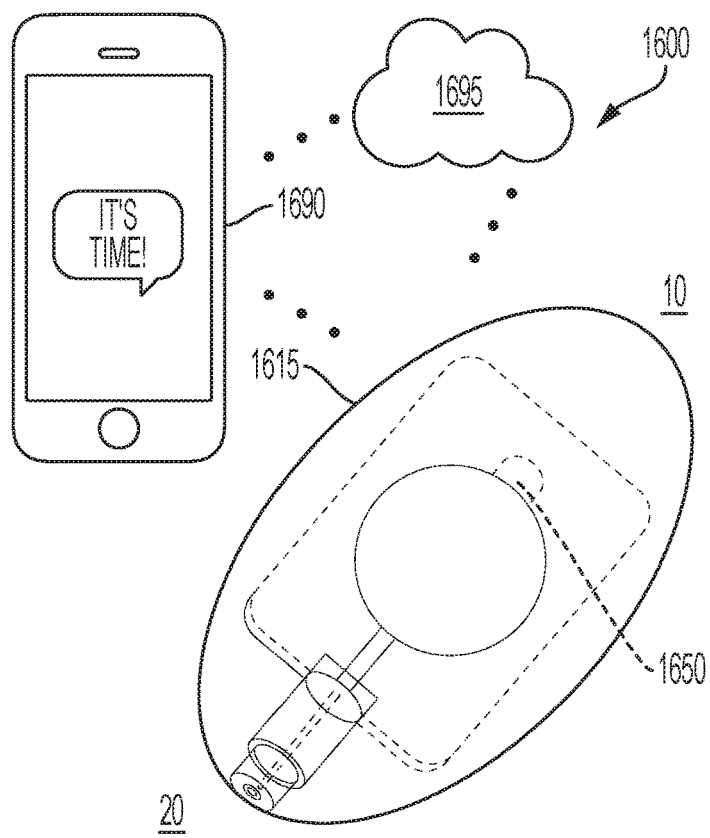
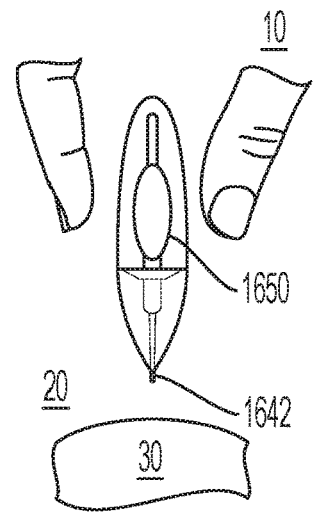
FIG. 16C
FIG. 16D

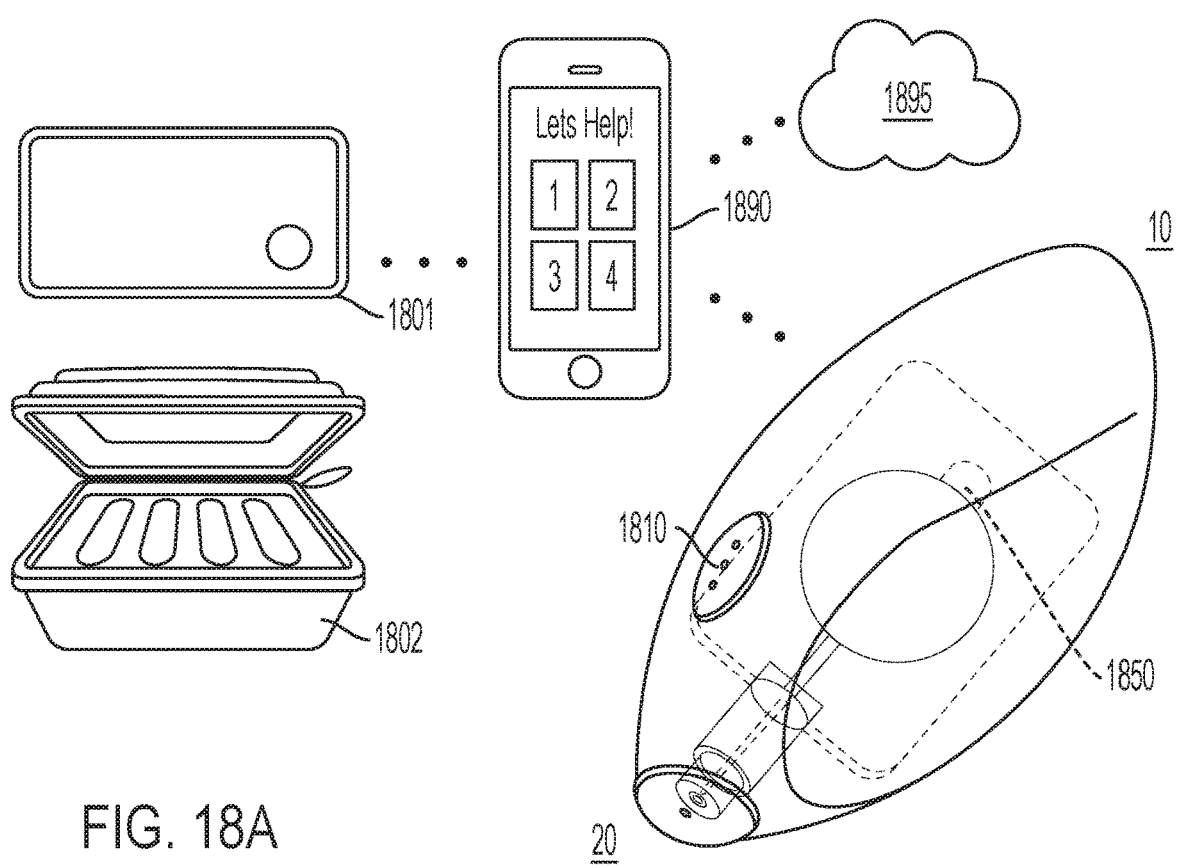
FIG. 18A
FIG. 18B
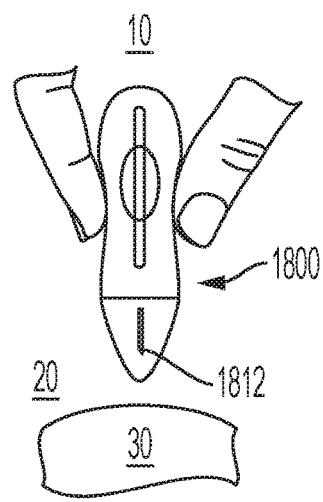
FIG. 18C

SYRINGES, SYRINGE CONTAINERS, KITS AND METHODS OF USE

CROSS-REFERENCE

This application claims the benefit of U.S. Provisional Application No. 62/845,475, filed May 9, 2019, entitled Injection Devices, Injection Containers and Methods of Use, and U.S. Provisional Patent Application No. 62/884,429 filed Aug. 8, 2019, entitled Injection Devices, Injection Containers and Methods of Use which applications are incorporated herein in their entirety by reference.

BACKGROUND

Field of the Invention

The present disclosure relates generally to a prefilled injection or syringe devices. More specifically, the disclosure relates to prefilled injection devices which contain medicaments.

Background

Prefilled injection devices provide healthcare workers a quick and efficient device for administering medicaments to patients. Prefilled injection devices can be particularly useful in remote locations.

What is needed are low-cost single-use injection devices that are safe, easy to use, and provide passive needle shielding and avoid patient's fear of needles.

SUMMARY

Injection or syringe devices are disclosed. The injection devices can be prefillable and provided in an all-in-one medicament delivery system for intramuscular or subcutaneous injections, or as separate components. Both healthcare workers and patients can use the injection devices for delivery of a wide variety of substances and medicaments used for medical treatment including, but not limited to, for example, vaccines, contraceptive medications (Levonorgestrel, Etonogestrel, Medroxyprogesterone), etc. Injection devices are configurable to use existing primary containers of medicaments.

Injection devices can reduce time to delivery, dosing errors, and provide more reliable drug concentration. The needle guard helps prevent patient anxiety associated with seeing the needle. The needle guard also protects against needle stick injury. Because the cap is not used to guard against the needle, replacing the cap after use does not risk accidental finger pricks.

An aspect of the disclosure is directed to injection devices for delivery a liquid medicament. Suitable devices comprise: a housing having a first end, a second end and an exterior surface wherein the housing defines a recess; a drug reservoir positionable within the recess; a cap engaging a first end of the housing; a press-point positioned on the exterior surface of the housing wherein the press-point is configured to engage the drug reservoir during use; a needle in communication with the drug reservoir extending from the second end of the housing; a needle guard; and a needle shield positioned within the needle guard. The injection devices can also include one or more of a removeable needle cover. a hinged panel on the exterior surface of the housing. In some configurations, the cap has a breakable seal. Additionally, the needle guard can be collapsible. The drug reservoir can be accessible via an aperture on the exterior surface of the housing. The press-point can further comprise a live hinge. A communicator can be provided that is configured to wirelessly communicate with a second device.

Another aspect of the disclosure is directed to methods of using an injection device to administer a liquid medicament. Suitable methods include providing an injection device comprising a housing having a first end, a second end and an exterior surface wherein the housing defines a recess, a drug reservoir positionable within the recess, a cap engaging a first end of the housing, a press-point positioned on the exterior surface of the housing wherein the press-point is configured to engage the drug reservoir during use, a needle in communication with the drug reservoir extending from the second end of the housing, a needle guard, and a needle shield positioned within the needle guard; pushing the cap in a distal direction to drive a proximal end of the needle through a seal; placing a distal end of the injection device adjacent a delivery surface; and applying pressure to the press-point. The injection devices can further comprise a needle cap, where there is a needle cap. The method can further comprise ones or more steps of removing the needle cap and twisting the cap of the injection device to break a seal. When the press point of the injection device comprises a live hinge the method can further comprise the step of applying pressure to the live hinge to achieve an audible click. The press point can have a first location and a second location which is configurable so that the press-point is lockable into a position when the live hinge has pressure applied.

Still another aspect of the disclosure is directed to kits comprising: a container; and an injection device comprising a housing having a first end, a second end and an exterior surface wherein the housing defines a recess, a drug reservoir positionable within the recess, a cap engaging a first end of the housing, a press-point positioned on the exterior surface of the housing wherein the press-point is configured to engage the drug reservoir during use, a needle in communication with the drug reservoir extending from the second end of the housing, a needle guard, and a needle shield positioned within the needle guard. The kits can also include one or more of instructions, and a calendar.

Yet another aspect of the disclosure is directed to a system for communicating information comprising: an injection device comprising a housing having a first end, a second end and an exterior surface wherein the housing defines a recess, a drug reservoir positionable within the recess, a cap engaging a first end of the housing, a press-point positioned on the exterior surface of the housing wherein the press-point is configured to engage the drug reservoir during use, a needle in communication with the drug reservoir extending from the second end of the housing, a needle guard, and a needle shield positioned within the needle guard, and one or more of a communicator, a controller, a memory and a power supply; and an electronic device in wireless communication with the injection device. In some configurations, the injection device is configurable to be in communication with a central location via the electronic device. The system can further be configured to communicate information from the central location to at least one of the electronic device and the injection device. Information can also be communicated from at least one of the electronic device and the injection device to the central location.

Another aspect of the disclosure is directed to an injection device for delivering a liquid medicament comprising: an openable housing having a first end, a second end and an exterior surface wherein the housing defines a recess configured to receive a liquid medicament delivery device comprising a body portion that surrounds a medicament reservoir, an outlet port that allows fluid to exit the reservoir, and a needle; a press-point positioned on the exterior surface of the housing wherein the press-point is configured to engage the medicament reservoir of the liquid medicament delivery device during use; an aperture through which the needle of the liquid medicament delivery device passes; and a needle cover. The injection device can further comprise a hinged shield. In some configurations, the needle cover has a breakable connection to the housing. Additionally, a visual needle depth indicator can be provided. One or more springs can also be provided between a first side of the housing and a second side of the housing. In some configurations, one or more sensors are also provided. A communicator can also be provided that is configured to wirelessly communicate with a second device. At least some devices also comprise one or more of a color change indicator, a temperature indicator, an LED, and a speaker.

In yet another aspect of the disclosure, a method of using an injection device to administer a liquid medicament is provided comprising: providing an injection device comprising an openable housing having a first end, a second end and an exterior surface wherein the housing defines a recess configured to receive a liquid medicament delivery device comprising a body portion that surrounds a medicament reservoir, an outlet port that allows fluid to exit the reservoir, and a needle, a press-point positioned on the exterior surface of the housing wherein the press-point is configured to engage the medicament reservoir of the liquid medicament delivery device during use, and an aperture through which the needle of the liquid medicament delivery device passes; inserting the liquid medicament delivery device into the recess in the injection device; placing a distal end of the injection device adjacent a delivery surface; and applying pressure to the press-point. A needle cap wherein may also be provided in which case the method further comprises the step of removing the needle cap.

Still another aspect of the disclosure is directed to a kit comprising: a container; and an injection device comprising an openable housing having a first end, a second end and an exterior surface wherein the housing defines a recess configured to receive a liquid medicament delivery device comprising a body portion that surrounds a medicament reservoir, an outlet port that allows fluid to exit the reservoir, and a needle, a press-point positioned on the exterior surface of the housing wherein the press-point is configured to engage the medicament reservoir of the liquid medicament delivery device during use, and an aperture through which the needle of the liquid medicament delivery device passes. The kit can also comprise one or more of instructions, and a calendar.

Still another aspect of the disclosure is directed to a system for communicating information comprising: an injection device comprising an openable housing having a first end, a second end and an exterior surface wherein the housing defines a recess configured to receive a liquid medicament delivery device comprising a body portion that surrounds a medicament reservoir, an outlet port that allows fluid to exit the reservoir, and a needle, a press-point positioned on the exterior surface of the housing wherein the press-point is configured to engage the medicament reservoir of the liquid medicament delivery device during use, and an aperture through which the needle of the liquid medicament delivery device passes; and an electronic device in wireless communication with the injection device. The system can further be configured to communicate information from the central location to at least one of the electronic device and the injection device. Information can also be communicated from at least one of the electronic device and the injection device to the central location.

Another aspect of the disclosure is directed to an injection device for delivering a liquid medicament comprising: a housing having a first end, a second end, an exterior surface and an ejector wherein the housing defines a recess configured to receive a liquid medicament delivery device comprising a body portion that surrounds a medicament reservoir, an outlet port that allows fluid to exit the reservoir, and a needle; a slider positioned on the exterior surface of the housing wherein the slider is configured to control a movement of the ejector within the housing and further wherein the ejector is configured to slidably engage the medicament reservoir of the liquid medicament delivery device during use; a removable cap; and an aperture through which the needle of the liquid medicament delivery device passes. The device can further comprise a color-changing ring. Additionally, in some embodiments, the ejector comprises a first hemi-circular side facing a second hemi-circular side with a gap along at least a portion of the length between the first hemi-circular side and the second hemi-circular side. A visual needle depth indicator can also be provided. In some configurations it may also be desirable to provide one or more sensors. A communicator configured to wirelessly communicate with a second device. One or more of a color change indicator, a temperature indicator, an LED, and a speaker can also be provided.

Yet another aspect of the disclosure is directed to a method of using an injection device to administer a liquid medicament comprising: providing an injection device comprising a housing having a first end, a second end, an exterior surface and an ejector wherein the housing defines a recess configured to receive a liquid medicament delivery device comprising a body portion that surrounds a medicament reservoir, an outlet port that allows fluid to exit the reservoir, and a needle, a slider positioned on the exterior surface of the housing wherein the slider is configured to control a movement of the ejector within the housing and further wherein the ejector is configured to slidably engage the medicament reservoir of the liquid medicament delivery device during use, a removable cap, and an aperture through which the needle of the liquid medicament delivery device passes; shaking the liquid medicament delivery device; inserting the liquid medicament delivery device into the recess in the injection device; placing a distal end of the injection device adjacent a delivery surface; and moving the slider in a distal direction. The method can also comprise the step of removing the cap.

Still another aspect of the disclosure is directed to a kit comprising: a container; an injection device comprising an injection device comprising a housing having a first end, a second end, an exterior surface and an ejector wherein the housing defines a recess configured to receive a liquid medicament delivery device comprising a body portion that surrounds a medicament reservoir, an outlet port that allows fluid to exit the reservoir, and a needle, a slider positioned on the exterior surface of the housing wherein the slider is configured to control a movement of the ejector within the housing and further wherein the ejector is configured to slidably engage the medicament reservoir of the liquid medicament delivery device during use, a removable cap, and an aperture through which the needle of the liquid medicament delivery device passes. One or more of instructions, and a calendar can also be provided.

Still another aspect of the disclosure is directed to a system for communicating information comprising: an injection device comprising a housing having a first end, a second end, an exterior surface and an ejector wherein the housing defines a recess configured to receive a liquid medicament delivery device comprising a body portion that surrounds a medicament reservoir, an outlet port that allows fluid to exit the reservoir, and a needle, a slider positioned on the exterior surface of the housing wherein the slider is configured to control a movement of the ejector within the housing and further wherein the ejector is configured to slidably engage the medicament reservoir of the liquid medicament delivery device during use, a removable cap, and an aperture through which the needle of the liquid medicament delivery device passes; and an electronic device in wireless communication with the injection device. The injection device can also be configurable to be in communication with a central location via the electronic device. In some embodiments, the system can be configured to communicate information from the central location to at least one of the electronic device and the injection device. The system can be further configured to communicate information from at least one of the electronic device and the injection device to the central location.

Another aspect of the disclosure is directed to an injection device for delivering a liquid medicament comprising: a housing having a first end, a second end, and a first arm, a second arm and a connector segment wherein the first arm and the second arm are connected via the connector segment at the first end and positioned substantially parallel to define a space between the first arm and the second arm configured to receive a liquid medicament delivery device comprising a body portion that surrounds a medicament reservoir, an outlet port that allows fluid to exit the reservoir, and a needle; and an aperture in the connector segment through which the needle of the liquid medicament delivery device passes. An insert can be provided that is positionable between the first arm and the second arm at the second end. At least some configurations also include one or more of a visual needle depth indicator and one or more sensors. Additionally a communicator can be provided that is configured to wirelessly communicate with a second device. One or more of a color change indicator, a temperature indicator, an LED, and a speaker can also be provided.

Yet another aspect of the disclosure is directed to a method of using an injection device to administer a liquid medicament comprising: providing an injection device comprising a housing having a first end, a second end, and a first arm, a second arm and a connector segment wherein the first arm and the second arm are connected via the connector segment at the first end and positioned substantially parallel to define a space between the first arm and the second arm configured to receive a liquid medicament delivery device comprising a body portion that surrounds a medicament reservoir, an outlet port that allows fluid to exit the reservoir, and a needle, and an aperture in the connector segment through which the needle of the liquid medicament delivery device passes; shaking the liquid medicament delivery device; inserting the liquid medicament delivery device into the space between the first arm and the second arm; placing a distal end of the injection device adjacent a delivery surface; and squeezing the device to cause the first arm to move towards the second arm. Additionally the method can comprise the step of removing the cap.

Still another aspect of the disclosure is directed to a kit comprising: a container; an injection device comprising a housing having a first end, a second end, and a first arm, a second arm and a connector segment wherein the first arm and the second arm are connected via the connector segment at the first end and positioned substantially parallel to define a space between the first arm and the second arm configured to receive a liquid medicament delivery device comprising a body portion that surrounds a medicament reservoir, an outlet port that allows fluid to exit the reservoir, and a needle, and an aperture in the connector segment through which the needle of the liquid medicament delivery device passes; and one or more of instructions, and a calendar.

Another aspect of the disclosure is directed to a system for communicating information comprising: an injection device comprising a housing having a first end, a second end, and a first arm, a second arm and a connector segment wherein the first arm and the second arm are connected via the connector segment at the first end and positioned substantially parallel to define a space between the first arm and the second arm configured to receive a liquid medicament delivery device comprising a body portion that surrounds a medicament reservoir, an outlet port that allows fluid to exit the reservoir, and a needle, and an aperture in the connector segment through which the needle of the liquid medicament delivery device passes; and an electronic device in wireless communication with the injection device. The injection device can also be in communication with a central location via the electronic device. The system is further configurable to communicate information from the central location to at least one of the electronic device and the injection device in some configurations. Additionally, the system is further configurable to communicate information from at least one of the electronic device and the injection device to the central location in some embodiments.

The fluid medicament for any of the disclosed devices, methods, kits or systems can be, for example, a vaccine or an active agent. Suitable active agents include a hormone used for the treatment of menopausal troubles or for contraception.

INCORPORATION BY REFERENCE

All publications, patents, and patent applications mentioned in this specification are herein incorporated by reference to the same extent as if each individual publication, patent, or patent application was specifically and individually indicated to be incorporated by reference.

U.S. Pat. No. 1,373,669A dated 1921 Apr. 5 for Hypodermic syringe;

U.S. Pat. No. 1,522,198A dated 1925 Jan. 6 for Hypodermic unit;

U.S. Pat. No. 1,668,588A dated 1928 May 8 for Hypodermic syringe;

U.S. Pat. No. 2,771,879A dated 1956 Nov. 27 for Disposable syringe;

U.S. Pat. No. 2,841,143A dated 1958 Jul. 1 for Injection device for liquids and ampoule therefor;

U.S. Pat. No. 2,876,771A dated 1959 Mar. 10 for Hypodermic syringes;

U.S. Pat. No. 2,907,326A dated 1959 Oct. 6 for Disposable syringe;

U.S. Pat. No. 3,989,045A dated 1976 Nov. 2 for Hypodermic syringe;

U.S. Pat. No. 4,410,323A dated 1983 Oct. 18 for Predosed disposable syringe;

U.S. Pat. No. 4,548,601A dated 1985 Oct. 22 for Prepackaged, injectable pharmaceutical and hypodermic needle combination;

U.S. Pat. No. 4,883,473A dated 1989 Nov. 28 for Single use injection device;

U.S. Pat. No. 5,261,881A dated 1993 Nov. 16 for Non-reusable dispensing apparatus;

U.S. Pat. No. 5,538,506A dated 1996 Jul. 23 for Prefilled fluid syringe;

U.S. Pat. No. 5,713,874A dated 1998 Feb. 3 for Camouflaged injection needle;

U.S. Pat. No. 6,120,478A dated 2000 Sep. 19 for Single Use syringe;

U.S. Pat. No. 6,656,147B1 dated 2003 Dec. 2 for Method and delivery device for the transdermal administration of a substance;

U.S. Pat. No. 7,115,108B2 dated 2006 Oct. 3 for Method and device for intradermally delivering a substance;

U.S. Pat. No. 8,377,029B2 dated 2013 Feb. 19 for Drug solution filling plastic ampoule and process for producing the same;

U.S. Pat. No. 9,265,889B2 dated 2016 Feb. 23 for Prefilled medical injection device; and U.S. Pat. No. 9,550,025B2 dated 2017 Jan. 24 for Injector.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 3E illustrates a cross-section of the injection device taken approximately at the line E/F shown in FIG. 1A;

FIG. 3F illustrates an interior view of the injection device taken approximately at the line E/F shown in FIG. 1A;

FIGS. 3G-H illustrate a needle guard at the distal end of the injection device of FIG. 1;

FIG. 8A is a top view of packaging containing the injection device; FIG. 8B is a side perspective view of packaging containing the injection device; FIG. 8C is a perspective top view of an injection device; and FIG. 8D is a side view of an injection device in use; FIG. 8E is a fluid delivery assembly;

FIG. 9A is a top view of the injection device; FIG. 9B is a side view of the injection device; FIG. 9C illustrates an internal mechanism of the injection device; and FIG. 9D is a side perspective view of an injection device in use;

FIG. 10A is a view of the packaging; FIG. 10B is a perspective view of the injection device which is in communication with an electronic device; and FIG. 10C is a side view of the injection device in use;

FIGS. 12A-C illustrate a kit (FIG. 12A) and a perspective view of another injection device (FIG. 12B); FIG. 12C illustrates the injection device in use;

FIG. 13A is a view of the packaging; FIG. 13B is a perspective view of the proximal end the injection device; FIG. 13C shows a perspective view of the injection device; and FIG. 13D is a side view of the injection device in use;

FIGS. 14A-C illustrate another exemplar injection device and system; FIG. 14A is a view of the packaging; FIG. 14B is a perspective view of the injection device; and FIG. 14C is a side view of the injection device in use;

FIGS. 16A-D illustrate another exemplar injection device and system; FIG. 16A is a view of the packaging; FIG. 16B is a front view of the injection device; FIG. 16C is a perspective view of an injection device which is in communication with an electronic device; and FIG. 16D is a side view of the injection device in use;

FIGS. 18A-C illustrate another exemplar injection device and system; FIG. 18A is a view of the packaging; FIG. 18B is a perspective view of the injection device which is in communication with an electronic device; and FIG. 18C is a side view of the injection device in use.

DETAILED DESCRIPTION

Figure 1C:
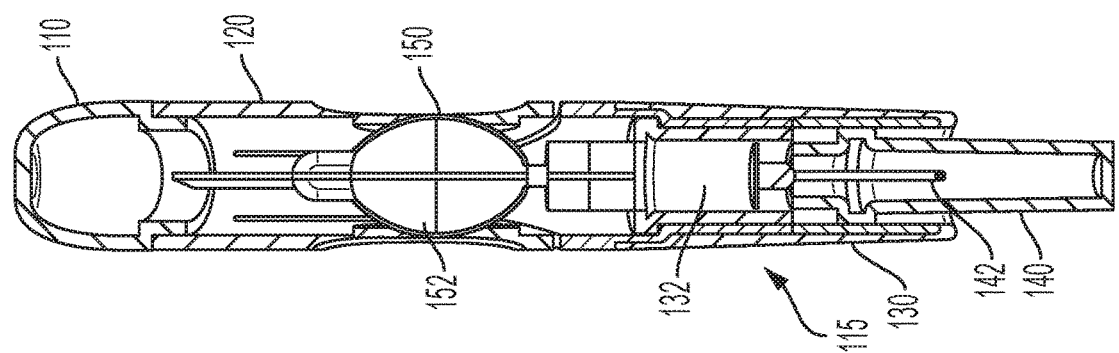
FIGS. 1A-C illustrate an exemplar injection device from an exterior view (FIG. 1A), from a cross-section (FIG. 1B), and an interior view (FIG. 1C)
Figure 1B:
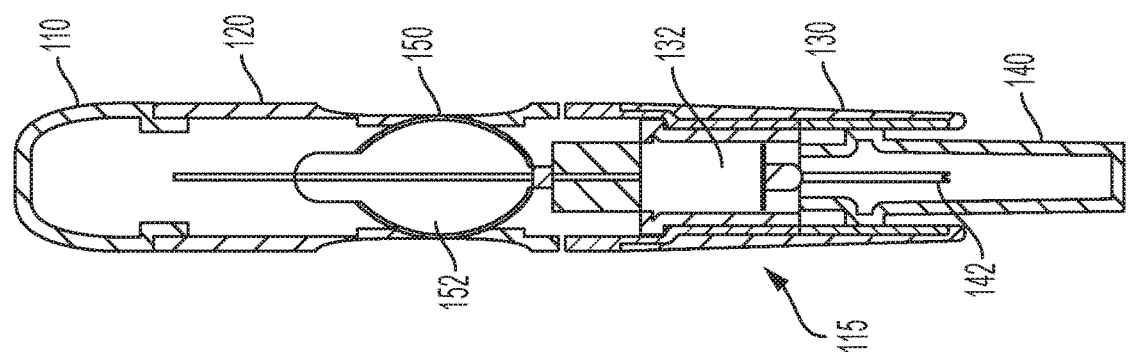
Figure 1A:
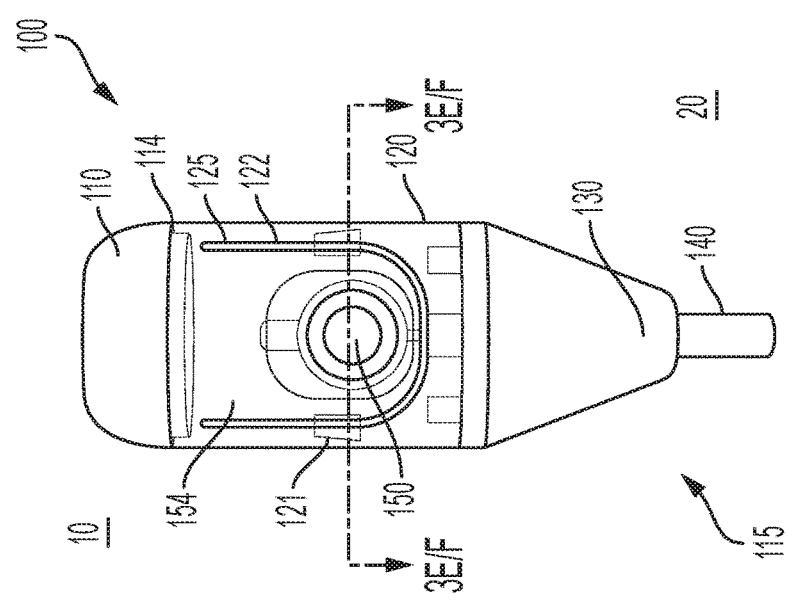

Turning now to the exemplar injection device 100 illustrated in FIGS. 1A-C, the injection device 100 has a proximal end 10 and a distal end 20. The injection device 100 is illustrated from a front face (as shown in FIG. 1A). The proximal end 10 is the end of the injection device 100 that is held by a user and the distal end 20 is the end of the injection device 100 that is positioned adjacent the injection site. The injection device 100 can be prefillable and single-use. As will be appreciated by those skilled in the art, the injection device 100 can be used by a healthcare practitioner to administer a medicament to a patient, or can be used by a patient to self-administer a medicament. Thus, a user can be a healthcare practitioner or a patient.

Starting from the proximal end 10 of the injection device 100, has a device cap 110, a body 120 which is part of the housing 115, a needle guard 130 and a needle cover 140. The components of the injection device 100 are formed integrally such that one or more components are formed as a single component or are formed to function as a single component once compiled.

The device cap 110 can have a seal lock at joint 114 for engaging the body 120. In some configurations, the device cap 110 cannot be removed from the body 120 without breaking. Breaking of the device cap 110 during removal provides a safety feature to prevent adulterating or refilling of a drug reservoir. Requiring the device cap 110 to break during removal also supports single use applications for the injection device 100. A press-point 150 or button is provided. During use, the user presses the press-point 150 to deliver the medicament from the fluid capsule 152, or drug reservoir, positioned within an interior of the housing 115 of the injection device 100.

In this embodiment, the body 120 is configurable to include a live hinge 122 on a first surface of the body 120. The live hinge 122 can be characterized as a hinge that flexes or moves even though it is part of a single component construction and formed integrally with the body 120. The live hinge 122 allows the press-point 150 to flex inward along an edge 125 to express all the medicaments contained in the fluid capsule 152. As will be appreciated by those skilled in the art, other types of hinges can be used without departing from the scope of the disclosure.

A needle guard 130 can be provided to shield a needle 142 (shown in FIG. 1B). The needle guard 130 engages a recessed lip 123 of the body 120. The needle 142 is positioned within the needle guard 130 which prevents the user from engaging the needle 142 prior to deployment. The needle guard 130 can be collapsible. In other configurations, the needle guard 130 can be rigid and spring loaded. The needle cover 140 passes through an opening in the needle guard 130. The needle exits the needle guard 130 when the press-point 150 is pressed by the user and the needle 142 is deployed to administer the medicament. The needle guard 130 locks a needle shield 132 in place after the injection is made and prevents the needle shield 132 from subsequently collapsing (or retracting, if rigid) thereby providing a passive mechanism to prevent needle sticks after use.

The press-point 150 can also be configured to lock a hinged panel 154 into place in an inward position at a locking interface 121 once the live hinge 122 is activated (i.e., pressing on the face of the device deflects the hinged panel 154 inward). Locking the hinged panel 154 into place prevents the hinged panel 154 from flexing outward to its original position once the user removes his or her finger from the press-point 150. This locking feature can be particularly useful when single use of the injection device 100 is desired. Once the press-point 150 reaches the correct inward position an audible and/or tactile 'CLICK' can also be experienced by the user. The audible and/or tactile feature lets the user know that the correct position has been reached and that all the medicament within the fluid capsule 152 was delivered to the patient.

A needle cover 140 can also be provided. The needle cover also 140 provides a convenient feature for a user to hold when deploying the injection device 100 as shown in FIG. 4. The needle cover 140 can be formed as part of a primary container in an aseptic manufacturing environment or formed separately. The needle cover 140 also maintains sterility of the needle during transit and protects the user from needle sticks prior to use of the injection device. During preparation for use, as discussed below, the user can perform any of the following steps: shaking the injection device 100, confirming an appearance of the medicament and lack of contaminants, and pushing on the needle cover 140 to drive the proximal end of the needle 160 through an internal septum thereby connecting the needle 160 to the medicament. The needle cover 140 is then removed and discarded. Once the needle cover 140 is removed, the injection device 100 can be deployed to administer the medicament to the patient.

Figure 2:
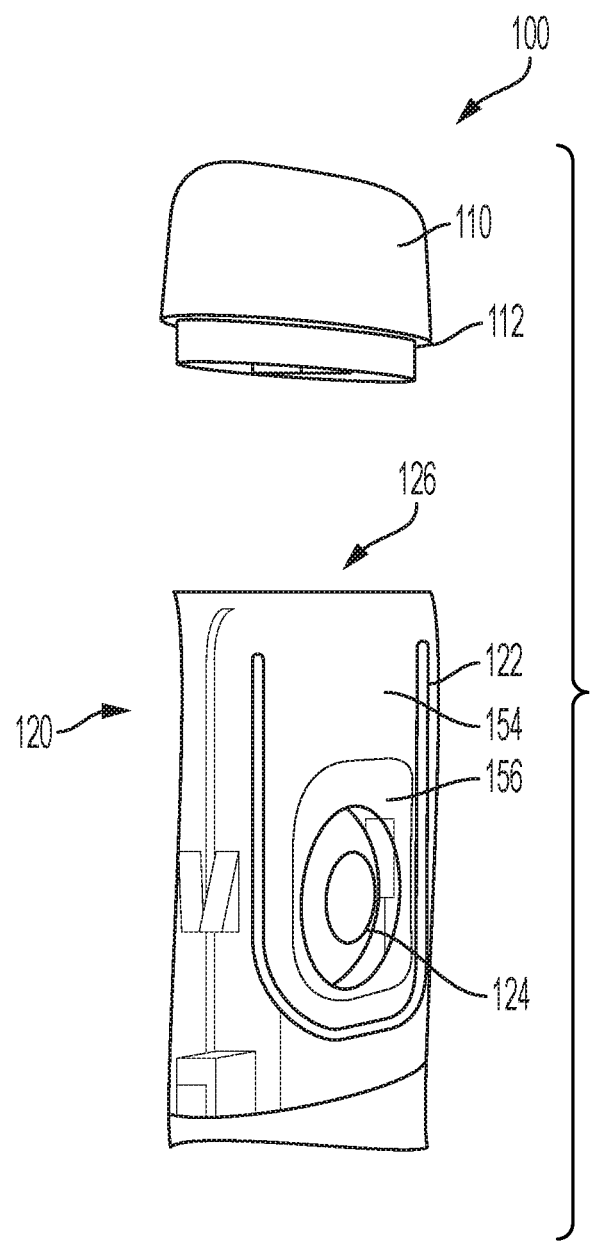
FIG. 2 illustrates the exemplar injection device of FIG. 1 from a perspective view with the cap removed.

FIG. 2 illustrates a top portion an exemplar injection device 100 from a perspective view with the device cap 110 removed. As illustrated, the device cap 110 has an indented surface 112 around an exterior surface of the device cap 110 at one end. The indented surface 112 provides an interface with the body 120 of the injection device 100 so that the indented surface 112 of the device cap 110 fits within an aperture 124 of the body 120. Once the device cap 110 is positioned so that the indented surface 112 fits within the aperture 124 of the body 120, a smooth exterior surface can be achieved between the device cap 110 and the body 120 in at least some configurations.

The hinged panel 154 can be configured to have a recess 156 which is curved to accept a finger (e.g. thumb) of a user. In one configuration, the recess 156 of the hinged panel 154 comprises an optically clear material which allows the user to view the medicament within the housing. An aperture can be provided in some configurations, that allow the user to view the medicament within the housing. The aperture can be provided within the recessed area or any other location on the housing adjacent to the fluid capsule.

Flat inner surfaces 126 can be provided within the recess 156 of the hinged panel 154. The flat inner surfaces 126 can interact with the inner medicament reservoir (fluid capsule 152) to completely express the medicament out of the fluid capsule when pressure is applied to the press-point 150 by the user. In some configurations, a snap or 'click' can be heard or felt by the user in some configurations as a confirmation to the user that the medicament has been completely expressed.

FIGS. 3A-J illustrate an exploded view of an injection device 100 as shown in FIGS. 1A-C and various detailed views and cross-sections including parts described above. A fluid capsule 152 is shown as rounded but can be almost any shape and is configurable to hold a suitable fluid within an interior of the fluid capsule 152. The fluid capsule 152 can be a primary medicament container obtained from a third party. The fluid capsule can be incorporated into the injection device 100 during the manufacturing process or inserted by a user prior to use.

An outlet 352 is provided at one end of the fluid capsule 152 which fits within a first tubular member 354. The first tubular member 354 engages a second tubular member 356 which surrounds a needle 142. The needle 142 fits within the outlet 352 of the fluid capsule 152 at a first proximal end 10 and is suspended within the body 120 at the second distal end 20. The fluid capsule 152, first tubular member 354, second tubular member 356 and needle 142 fit within the body 120 of the injection device 100.

A seal or septum (not shown) can be provided between the proximal end of the needle 142 and medicament housed within the fluid capsule 152.

As shown in step 2 in FIG. 4, in some uses the device cap 110 is pushed backward driving the proximal end of the needle 160 through the seal/septum until a click is heard. This lets the user know they have pushed the device cap 110 back far enough and then can remove and discard the needle cover 140.

The body 120 can have a viewer 370 on a front face 302. When the fluid capsule 152, first tubular member 354, second tubular member 356, and needle 160 are positioned within the body 120, a portion of the fluid capsule 152 can be visualized through the viewer 370 in the body 120. The viewer 370 allows the user to see the medicament within the fluid capsule 352. The viewer 370 can be, for example, a transparent, or substantially transparent, portion of the housing 115, an aperture in the housing, or a housing which is entirely transparent or substantially transparent. Other mechanisms for providing a viewing function can be used without departing from the scope of the disclosure.

A needle shield 132 can be provided to protect the needle 142 during use. The shield 132 can extend from the body 120 of the injection device 100 housing 115. A lock 126 is positionable around the needle shield 132 and fits within an interior of the needle guard 130.

Figure 3A:
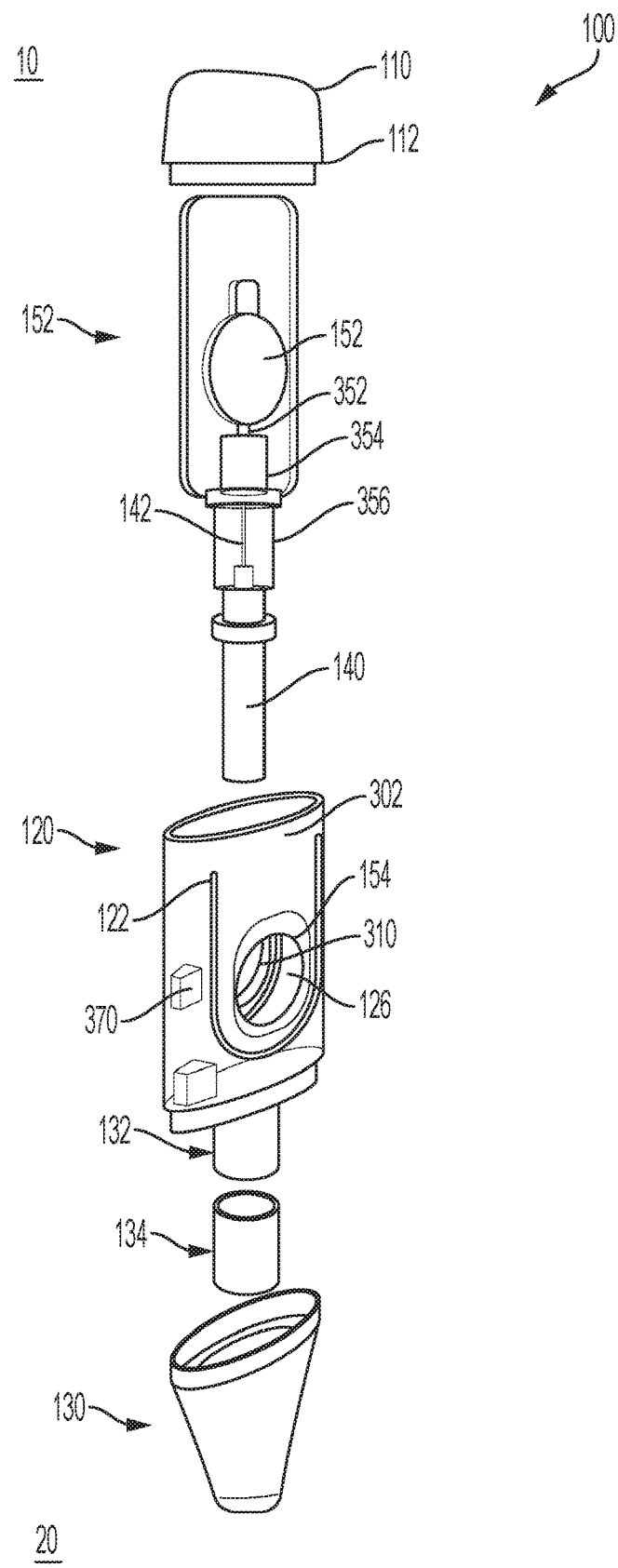
FIG. 3A illustrates an exploded view of the injection device of FIG. 1.
Figure 3B:
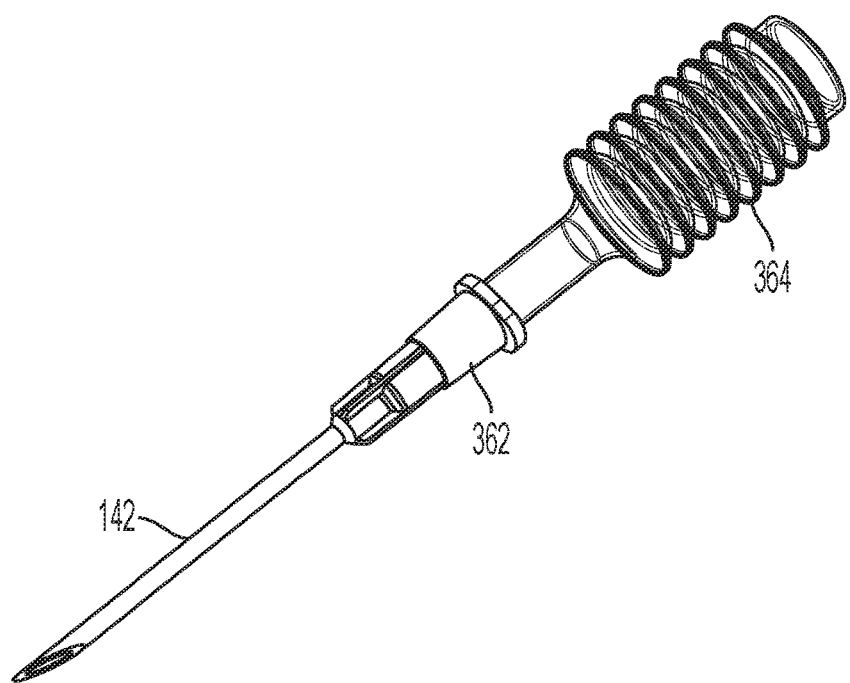
FIG. 3B illustrates a needle with bellows suitable for use with the disclosed injection devices.

The needle 142 is a hollow tubular member as shown in FIG. 3B. The skin piercing distal end of the needle 142 can slant at an angle to provide a pointed end for commencing the insertion process. The size of the needle can be, for example, gauge 20 to 27.

The needle 142 configuration illustrated in FIG. 3B, is an alternate embodiment to using the fluid capsule 152 assembly shown in FIG. 1. Bellows 364 can be provided which are made from a soft, moldable polymer. The bellows 364 forms an interior reservoir which holds the medicament. A lug or Luer 362 can be provided as part of the needle assembly to secure the bellows 364 and the needle 142.

Figure 3C:
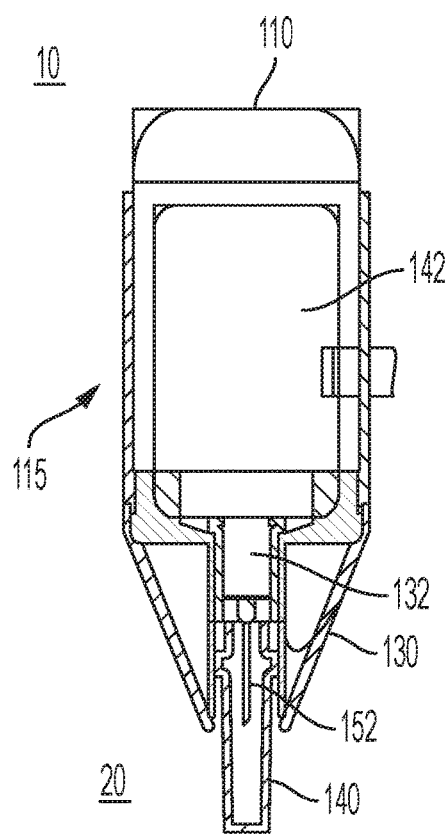
FIG. 3C illustrates a cross-section of the injection device of FIG. 1.

FIG. 3C is a cross-section of an injection device 100 with a suitable capsule 142 for use in the injection device 100 of FIG. 3A. The capsule 152 contains the medicament. The capsule 152 fits within an interior cavity of the housing 115 of the injection device 100. A distal end 20 of the capsule 152 is configured to engage the needle 152 of the injection device 100.

Figure 3D:
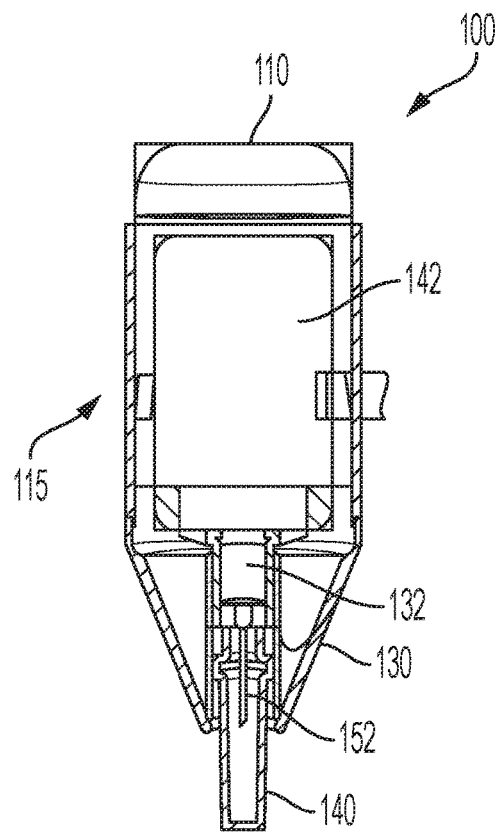
FIG. 3D illustrates an interior view of the injection device of FIG. 1.

FIG. 3D is an interior view of the injection device 100 with the capsule 152 for use in the injection device of FIG. 3A.

FIG. 3E illustrates a cross-section of the housing 115 of the injection device 100 taken along the line E/F in FIG. 3A. FIG. 3E also illustrates the capsule 152 positioned within an interior cavity of the housing 115 of the injection device 100. The capsule 152 has a flange 310 extending from either side.

FIG. 3F is an interior view (looking into the housing 115 of the injection device 100) from the cross-section taken along the line E/F in FIG. 3A. The flanges 310 of the capsule 152 are positioned between a first plate 320 and a second plate 322. The two plates extend from an interior surface of the housing. The gap between the two plates is sized to securely receive the flange of the capsule. This feature secures the capsule 152 within the interior of the housing.

Turning to FIGS. 3G-H, a locking mechanism can be provided. The locking mechanism 380 provides a lock, e.g., an inner rigid tubular member, which allows the needle shield 132 to engage the needle guard 130. The needle shield 132 allows the compression of the needle guard 130 once after which the needle shield 132 locks into place once the injection device 100 is removed from the skin. Locking the needle shield 132 into place preventing subsequent needle sticks.

Figure 3I:
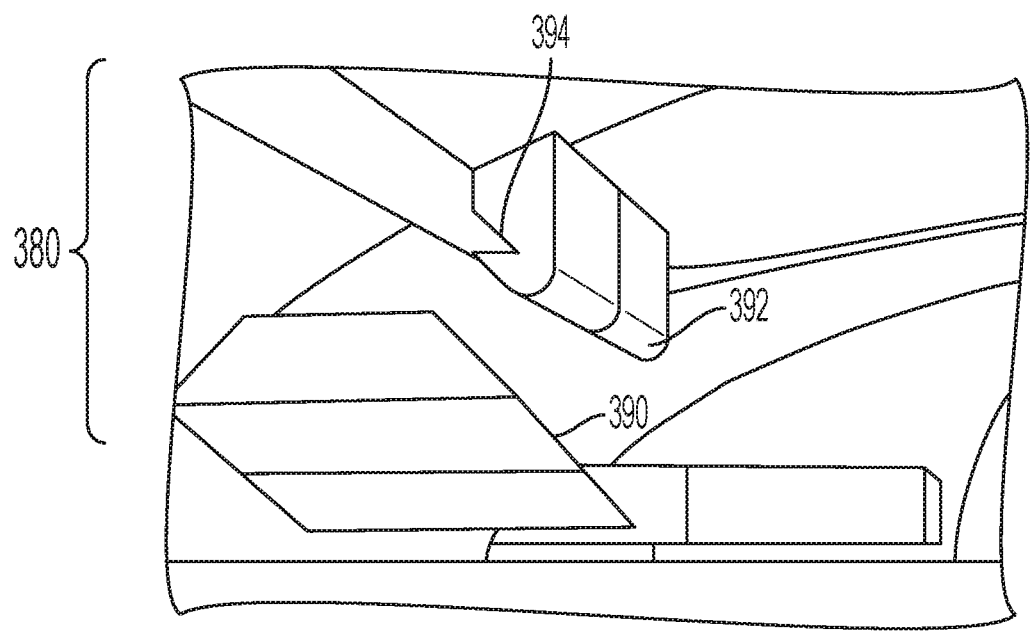
FIGS. 3I-J illustrate an exemplar snap lock interface.
Figure 3J:
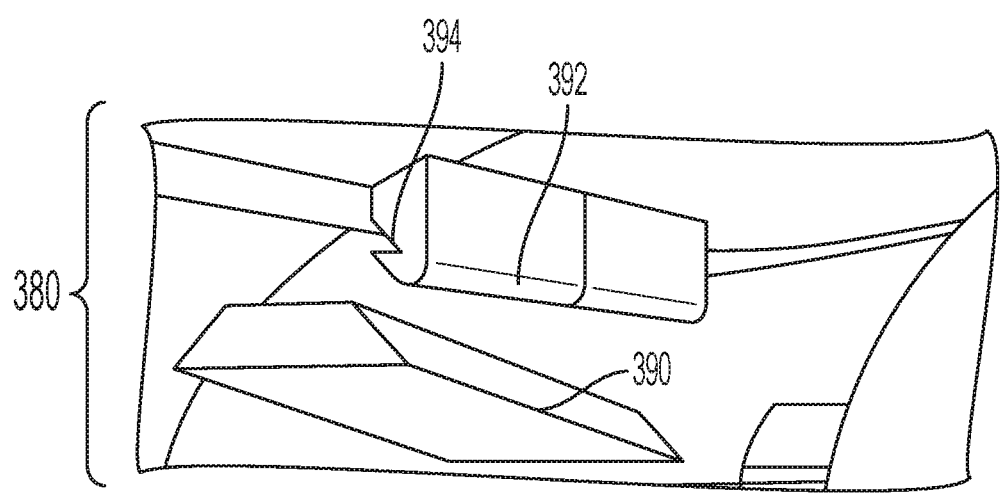

FIGS. 3I-J illustrate a snap-lock interface 380 which allows two surfaces of the injection device 100 to be secured. A first surface 390 has an angled face which faces the second surface 392. The second surface 392 has a groove 394 which is configured to mate with the angled face of the first surface 390. When the two surfaces mate, the surfaces are locked together and click to form a secure engagement. The snap-lock interface can be used at a variety of locations in the injection device 100, including the locking mechanism shown in FIGS. 3G-H, and the locking interface between the live hinge and the body shown in FIG. 1A, to name a few. Other locking mechanisms, such as detents, can be used without departing from the scope of the disclosure.

Figure 4C:
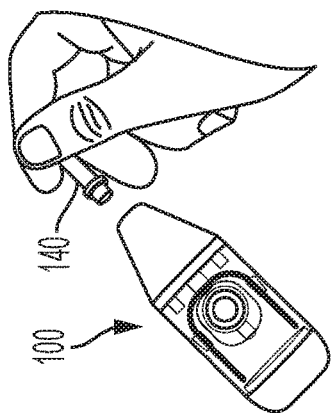
FIGS. 4A-F illustrates a method of using the exemplar injection device of FIG. 1.
Figure 4F:
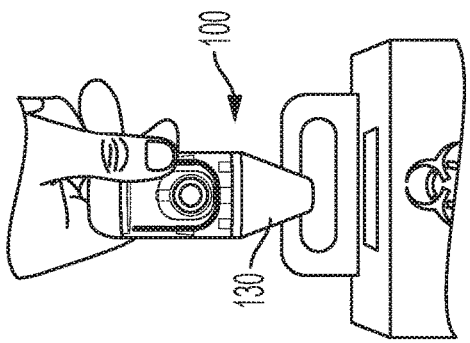
Figure 4B:
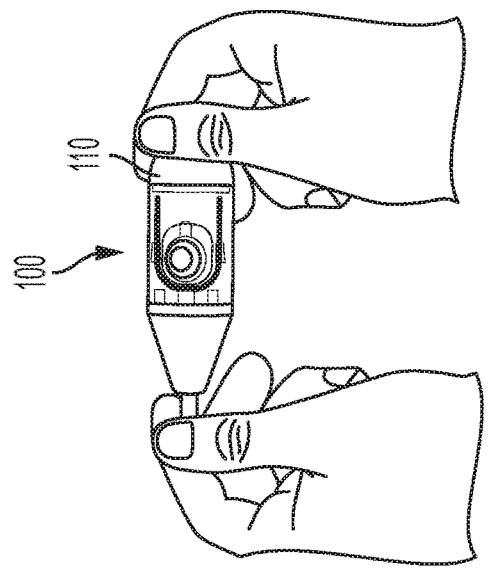
Figure 4E:
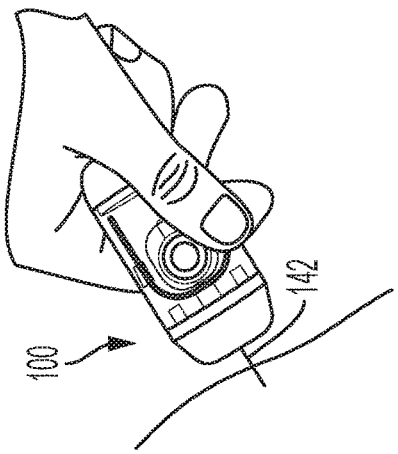
Figure 4A:
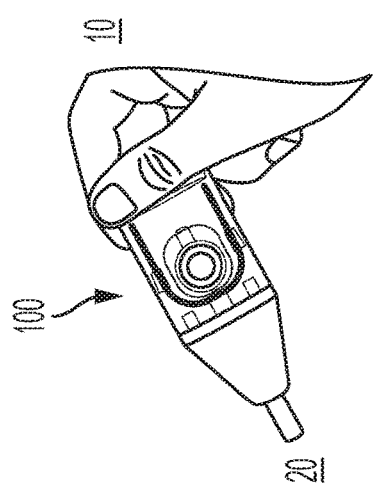
Figure 4D:
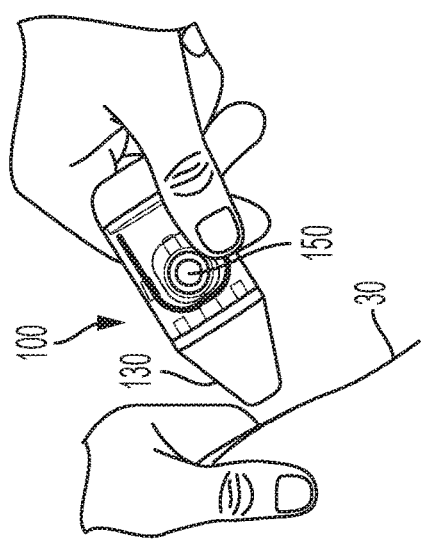

FIGS. 4A-F illustrates select steps in a method of using the exemplar injection device 100 of FIG. 1. Once the injection device 100 is put together, in one embodiment, the user shakes the injection device 100 to homogenize the liquid within the fluid capsule 152 (FIG. 4A). Once the fluid is homogenized, the user verifies that the fluid is uniform, the correct color and free from contaminants visible with the human eye. The user then grasps the injection device 100 by grasping a proximal end 10 with one hand and a distal end 20 with the other hand and twists to break the seal (FIG. 4B). Once the injection device 100 is grasped and the seal is broken, the user pushes the cap 110 in a distal direction until, for example, the cap 110 makes a clicking sound (FIG. 4B) or will not move distally. Pushing the cap 110 toward the distal end 20 drives the proximal end of the needle 160 thru the seal/septum. Once the user hears a clicking noise, the needle cover 140 is removed (FIG. 4C). Removing the needle cover 140 does not expose the user to the needle 160 as shown in FIG. 4C. After removing the needle cover 140, the distal end 20 of the injection device 100 is placed against the skin of a recipient with enough pressure to collapse or retract the needle guard 30 as shown in FIG. 4D. The user then applies pressure to the press-point 150 (i.e., presses on the press-point) until a clicking noise is heard to inject the fluid (FIG. 4E). During the injection process, the user and/or the patient cannot see the needle 160 being administered through the needle guard 130. Once the fluid is delivered the entire injection device 100 can be discarded as shown in FIG. 4F.

As will be appreciated by those skilled in the art, fewer or additional steps might be employed without departing from the scope of the disclosure. For example, shaking to homogenize the liquid may not be required in some embodiments. Twisting to break a seal may also not be required. The user may or may not hear clicking at various times during the process. Additional steps can include taking a photo of the medicament. Using a photo would allow a user to achieve a view of the clarity of the medicament that is better than a human visual inspection. Additionally, in some configurations, the photo can be transmitted to another location for evaluation by, for example, a healthcare provider to assess one or more of the uniformity of the fluid, the color of the fluid, and/or the contamination of the fluid (e.g., existence of particulate matter).

Figure 5C:
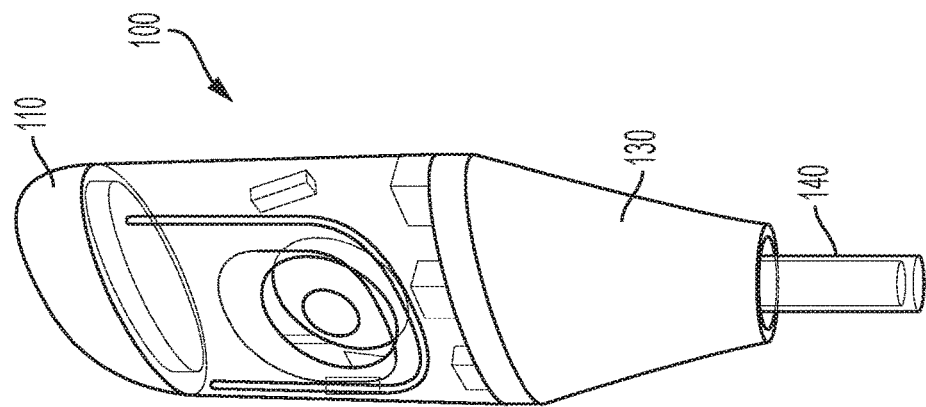
FIGS. 5A-C illustrates the exemplar injection device of FIG. 1 from a first perspective view, a side view and a second perspective view.
Figure 5B:
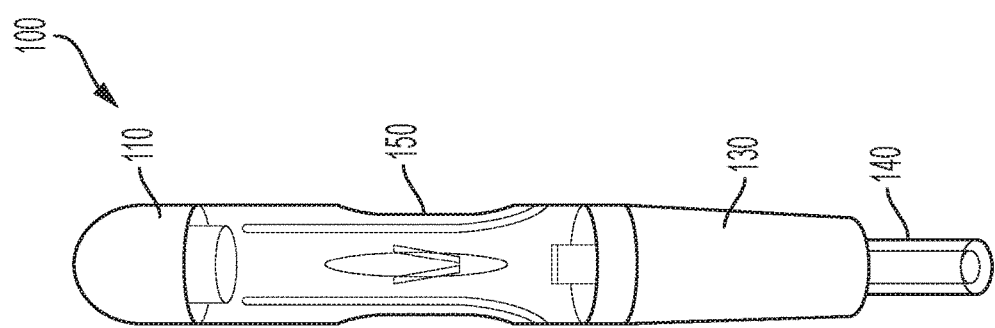
Figure 5A:
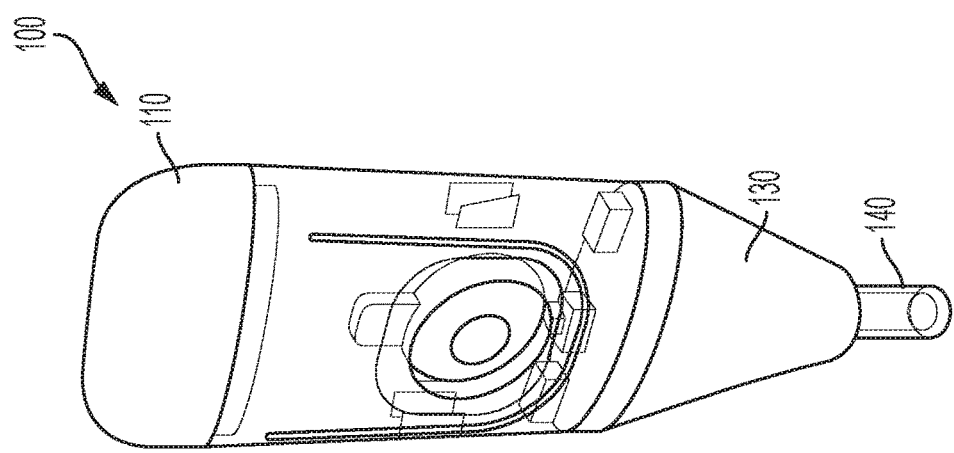

FIGS. 5A-C illustrates the exemplar injection device 100 of FIG. 1A from a first perspective view, a side view and a second perspective view. The injection device 100 has a cap 110, a needle guard 130, a needle cover 140, and a press-point 150. Suitable dimensions allow for an elongated body with parallel sides along a length with a wider front face (FIGS. 5A and 5C) and a slimmer side view (FIG. 5B). The distal end 20 can be configured to taper to the needle cover 140.

Figure 6:
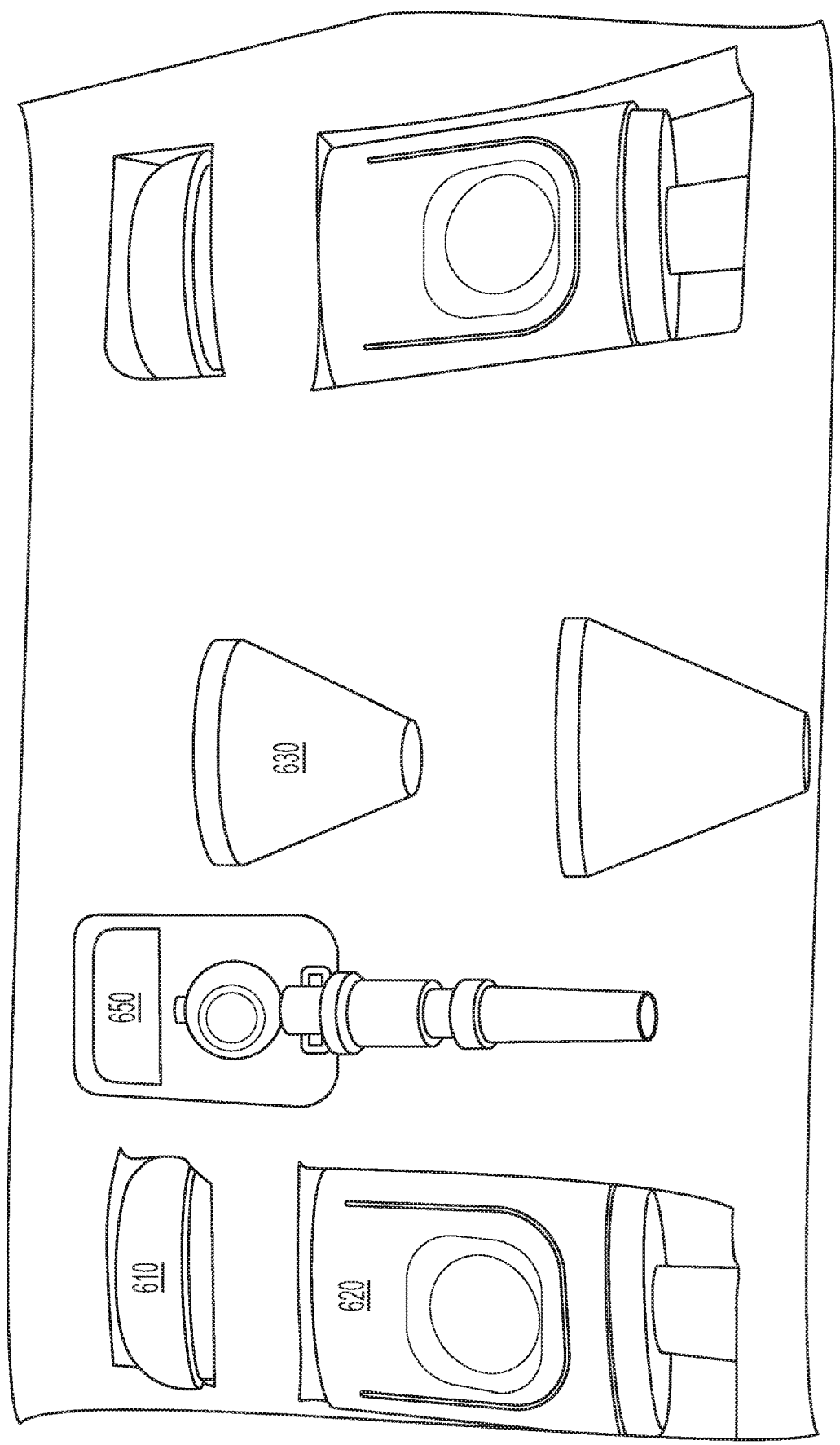
FIG. 6 illustrates a kit of component parts for the injection device.

FIG. 6 illustrates a kit for user assembly comprising the cap 610, a body 620, a fluid delivery assembly 650, and a needle guard 630. Kit assemblies may be useful in some geographic areas where the device may be deployed. The kit can also include instructions and/or a calendar.

Figure 7:
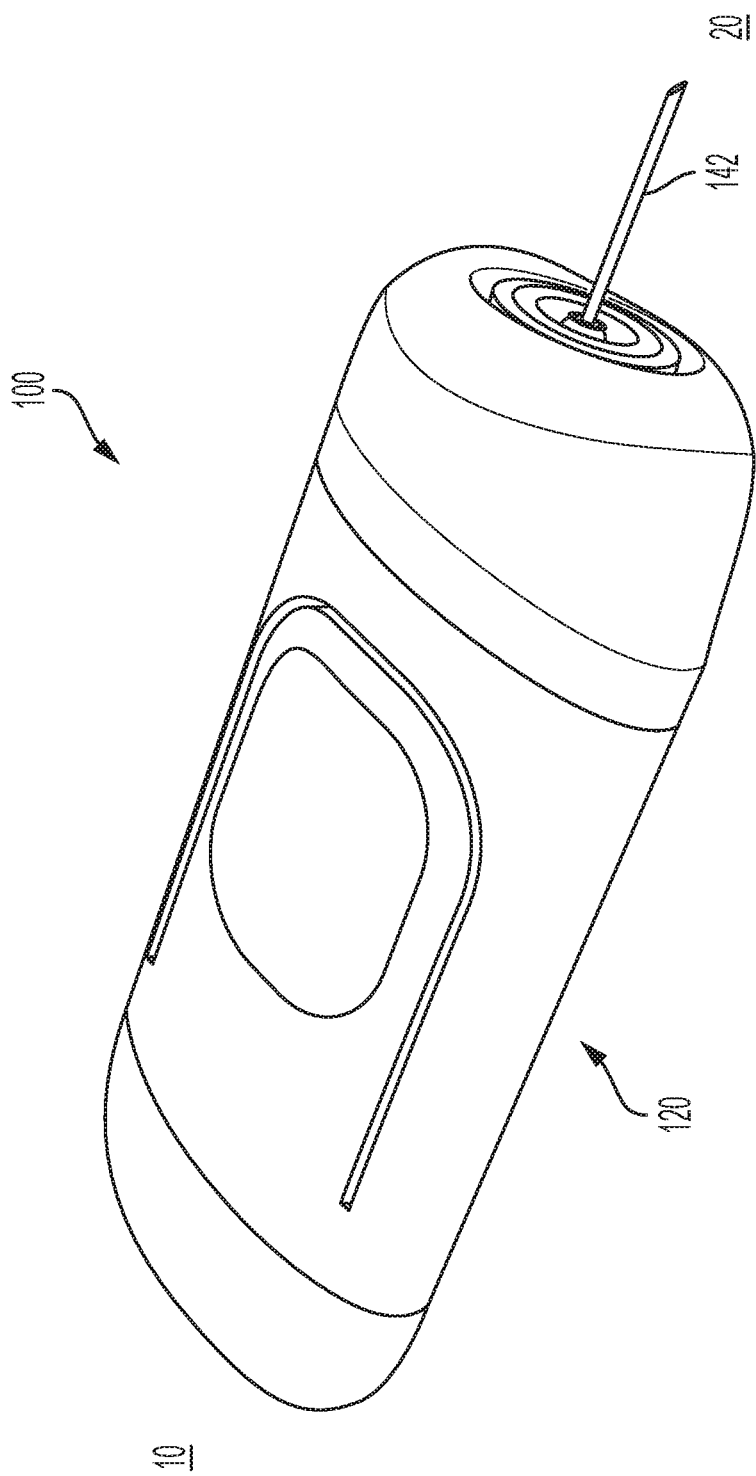
FIG. 7 illustrates an alternative embodiment of an injection device.

FIG. 7 is another configuration of an injection device 100 where the body 120 of the injection device 100 has an elongated oval shape. The needle 142 is shown extending from the distal end 20 without a needle cover.

Figure 8A:
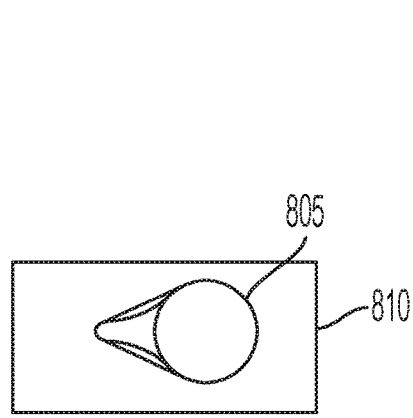
FIGS. 8A-E illustrate an exemplar injection device and system.
Figure 8B:
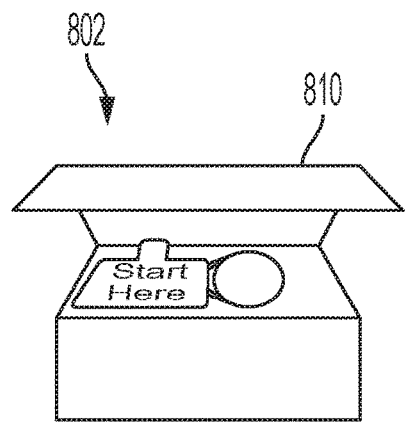
Figure 8C:
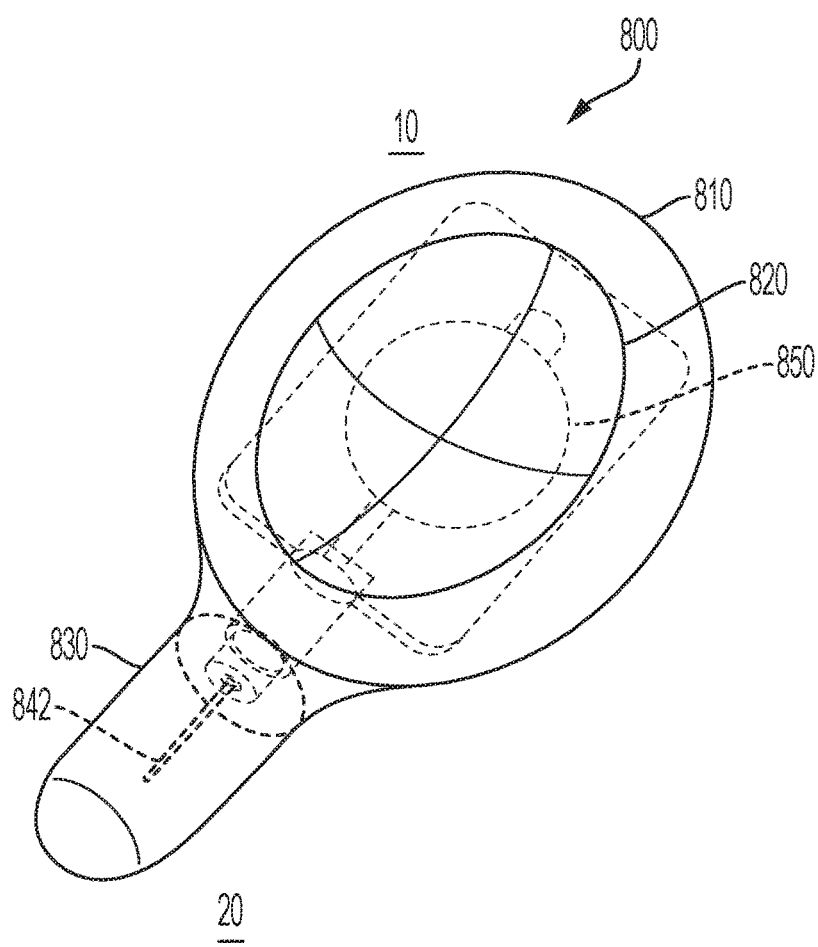
Figure 8D:
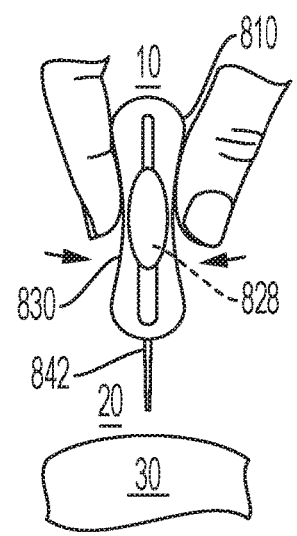

Turning now to the exemplar injection device 800 illustrated in FIGS. 8A-D, the injection device 800 has a proximal end 10 and a distal end 20. The proximal end 10 is the end of the injection device 800 that is held by a user and the distal end 20 is positionable adjacent the injection site 30 as shown in FIG. 8D. As will be appreciated by those skilled in the art, the injection device 800 can be used by a healthcare practitioner to administer a medicament to a patient, or can be used by a patient to self-administer a medicament. Thus, as with other embodiments, a user can be a healthcare practitioner or a patient.

The injection device 800 can be provided in a package 802 as shown in FIG. 8B. The package 802 can be a rectangular box (as illustrated) with a lid 810 that opens to reveal the injection device 800. The lid 810 can have a surface image 805 as shown in FIG. 8A. The surface image 805 can configured to be useful in instructing a user on use of the injection device during deployment. The injection device 800 is designed to be used in conjunction with a fluid delivery device, such as the fluid delivery assembly shown in FIG. 8E.

Starting from the proximal end 10 of the injection device 800 shown in FIG. 8C, a housing 810 is provided. The housing 810 has a spring-loaded button 820 positionable on a front face of the housing 810. The housing 810 has an internal cavity for housing a fluid delivery assembly 850 or capsule. A needle guard 830 can be provided which surrounds the needle 842. The needle guard 830 can be removable. A larger cap can be provided which improves ease of removal of the needle guard 830. The spring-loaded button 820 can have a dimensional shape that approaches the dimensional shape of a surface of the injection device 800.

The components of the injection device 800 can be formed integrally such that one or more components are formed as a single component or function as a single component once compiled.

During use, as shown in FIG. 8D the user grasps the injection device 800 and presses on the spring-loaded button 820 which ejects fluid contained within a capsule 828 of the injection device 800 into the tissue at an insertion area 30 of the recipient.

In one configuration, the needle guard 830 is removed prior to pressing the spring-loaded button 820. In another configuration, pressing the spring-loaded button 820 advances the needle distally beyond the end of the needle guard 830 into the insertion area 30 (e.g., tissue) and ejects the fluid from the capsule 828 or fluid reservoir into the tissue 30. Additionally, the spring-loaded button 820 can be positioned on a single surface of the injection device 800 or on two opposing surfaces, e.g., on a top surface (upper surface) or on a top surface and a bottom surface (lower surface). When the spring-loaded button 820 is positioned on opposing surfaces of the injection device 800 pressure is applied to both sides of the capsule 828 during use.

Figure 8E:
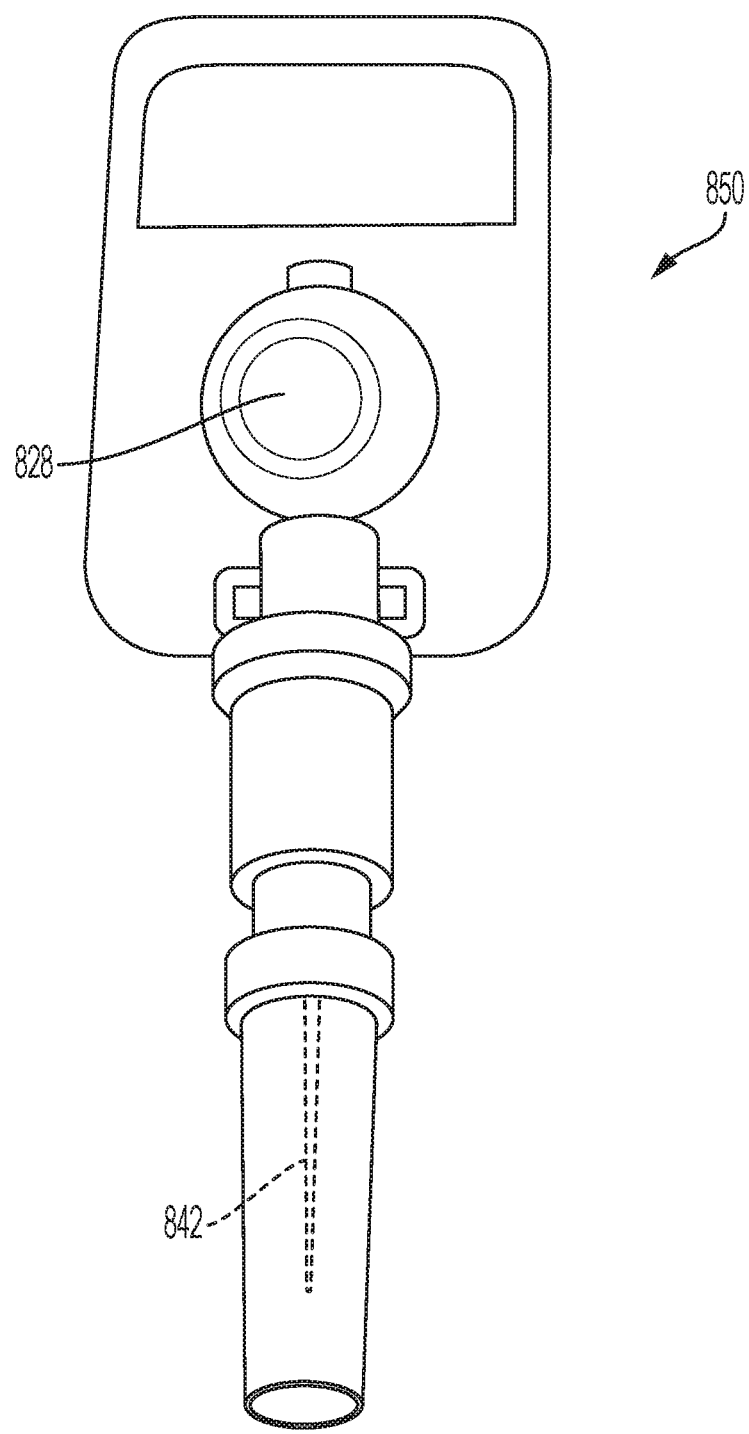

FIG. 8E is a fluid delivery assembly 850 suitable for use in a variety of the injection device configurations illustrated. The fluid delivery assembly 850 has a rectangular portion with a capsule 828 or fluid reservoir configured to hold a medicament. An elongated sleeve or extension extends from one end of the rectangular portion. The extension has a flange houses a hub and a needle 842. A limiter can be provided which engages the hub and surrounds a portion of the needle. The fluid delivery assembly 850 is positionable within an interior of the injection device 800 and is shown in shadow in FIG. 8C.

Figure 9B:
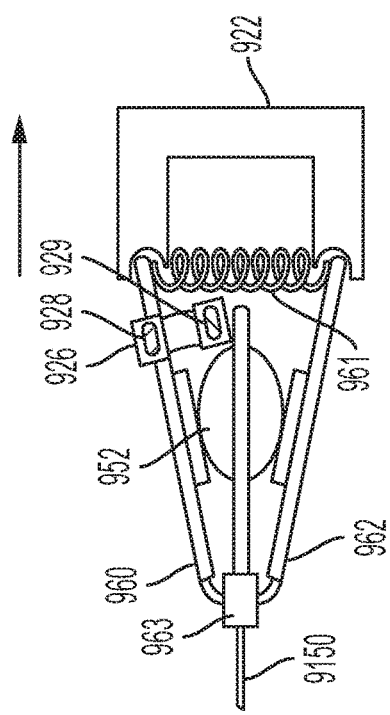
FIGS. 9A-D illustrate another exemplar injection device and system.
Figure 9D:
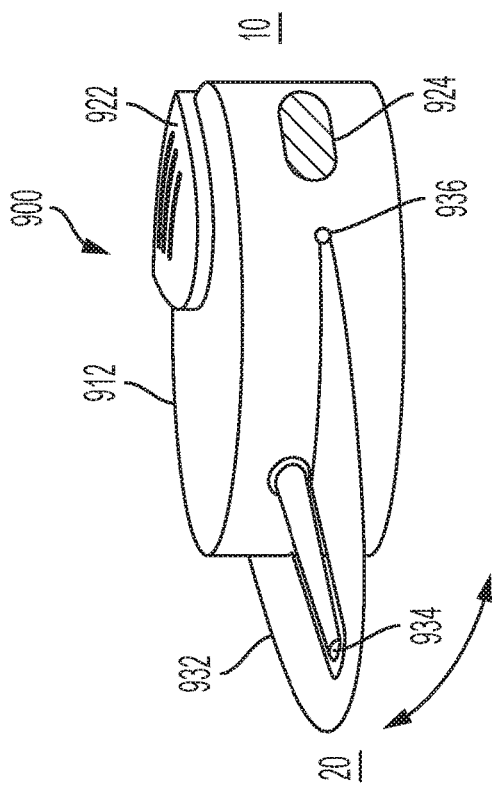
Figure 9A:
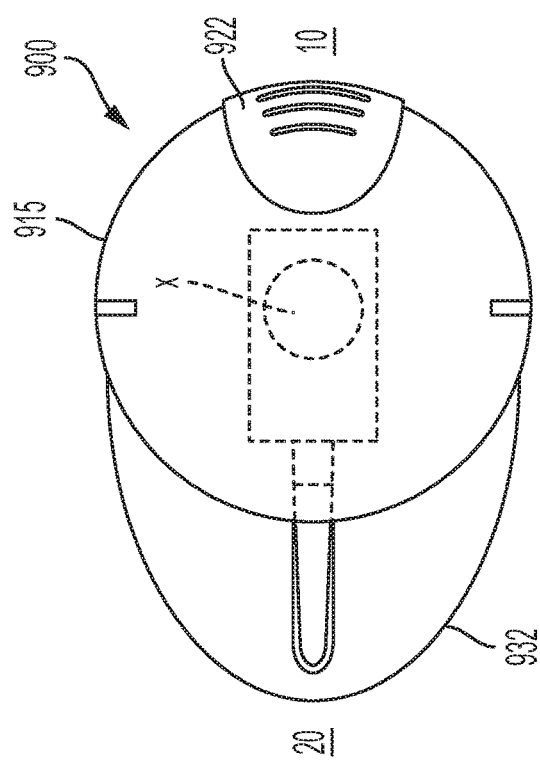
Figure 9C:
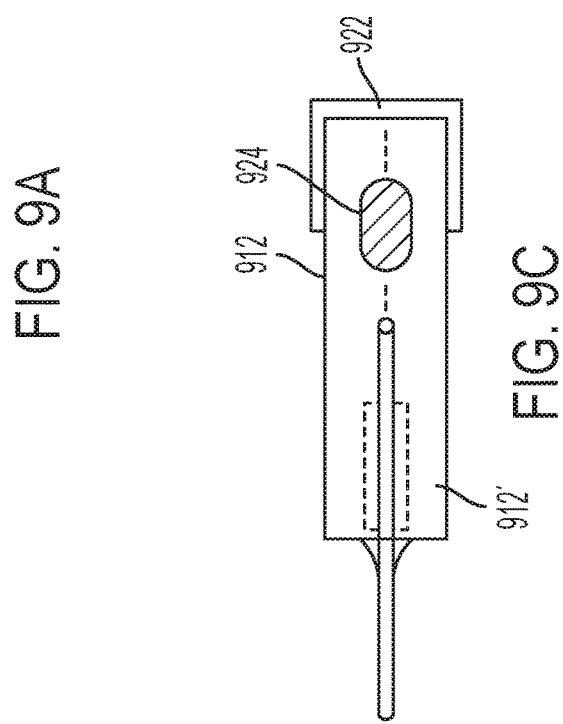

FIGS. 9A-D illustrate another exemplar injection device 900 suitable for use with a fluid delivery assembly. The injection device 900 has a housing 915 with round (circular) shape in a first dimension as shown in FIG. 9A and flat sides 912, 912', or substantially flat sides, in a second dimension as shown in FIG. 9C. The flat sides 912, 912' shown in FIG. 9C could also be curved, outward (convex) or inward (concave) in other embodiments and may be parallel or substantially parallel. Additionally, the round shape shown in FIG. 9A can be oval, ovoid, square, rectangular, or any other suitable shape without departing from the scope of the disclosure.

A flip guard 932 is provided. In a first position, the flip guard 932 is positioned so that it presents a surface adjacent a needle exit 934. In a second position, the flip guard 932 rotates from a hinge 936 (with a hinge on either side of the device) so that the needle exit 934 is exposed.

A slide button 922 is provided which is retracted away from a central position x on the surface of the injection device 900. As shown in FIG. 9BC, two angled levers 960, 962 have a connection point 963 at one end and are separated by a spring 964 at an opposing end. When the slide button 922 is retracted, the space between the two angled levers 960, 962 is reduced, pressure is placed on the capsule 952 that holds the medicament. The spring 964 is positioned between the two angled levers 960, 962 at one end. The spring 964 provides injection force. The force applied to the angled levers 960, 962 ensures that the liquid contents within the reservoir are ejected to achieve the required dosage. As will be appreciated by those skilled in the art, some residual liquid may remain within the capsule 952 after the force is applied. However, any residual would be contemplated as part of achieving an administration of a required or intended dosage.

An indicator window 924 is provided. When the medicament is ejected, an indicator window insert 926 changes position so that the user is provided visual feedback confirming that the injection process is complete. The indicator window insert 926 has a first surface 928 and a second surface 929. In one embodiment each of the surfaces have a different color so that when one surface is presented, a first color appears in the indicator window, when the second surface is presented a second color is presented which is visually different from the first color. Once the medicament is delivered the second surface is presented to indicate that the delivery process is completed. Other strategies can be employed to result in a first visual indicator and a second visual indicator.

Figure 10C:
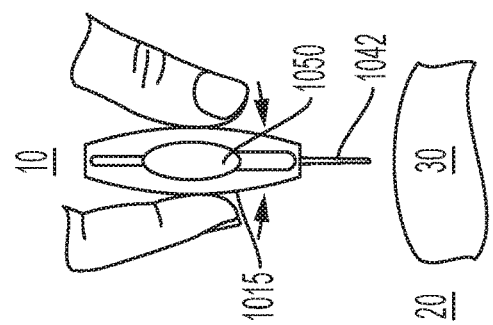
FIGS. 10A-C illustrate another exemplar injection device and system.
Figure 10B:
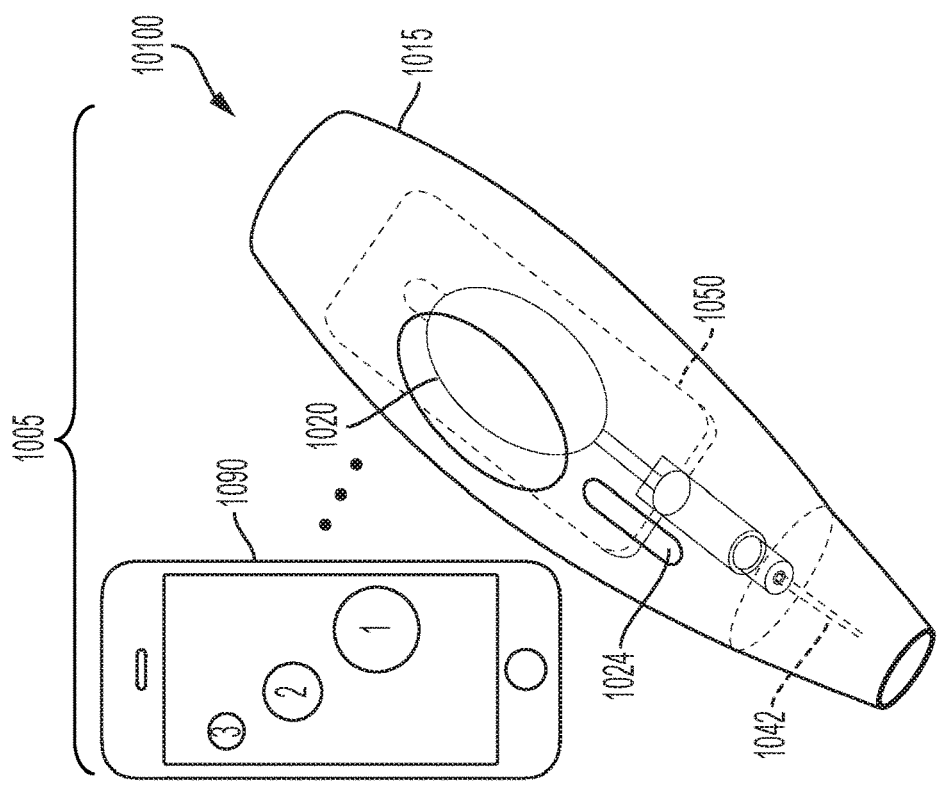
Figure 10A:
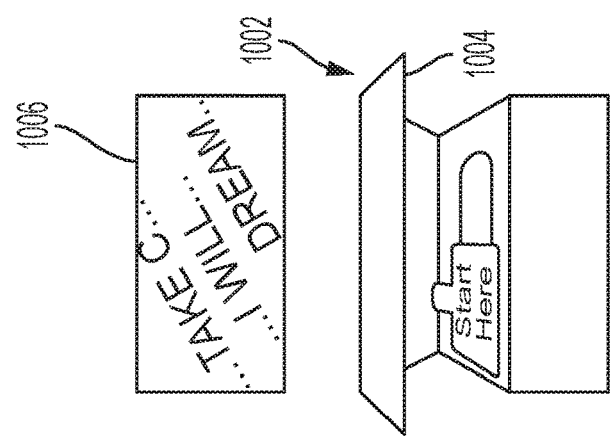

FIGS. 10A-C illustrate another exemplar injection device 1000 suitable for use with a fluid delivery assembly and system 1005. FIG. 10A is a view of packaging 1002 suitable for housing 1015 the injection device 1000 and associated materials, such as instructions for use. A surface image 1006 can be provided on the lid 1004 of the packaging 1002, as shown.

FIG. 10B is a perspective view of the injection device 1000 having a housing 1015 with an elongated form with rounded sides. A visual indicator such as a color changing window 1024 can be provided. The color changing window 1024 changes from a first color when the capsule 1028 is filled to another color when the capsule 1028 is empty. The fluid delivery assembly 1050 is shown positioned within the injection device 1000.

The injection device 1000 is configurable to include suitable electronics to enable the injection device 1000 to communicate with an electronic device 1090. Where the injection device includes electronics to enable communication with an electronic device, the injection device 1000 can further be configured to be part of a system which is in communication with a central location, such as via the electronic device 1090. Suitable electronics, power supply, and memory components will be included in the injection device 1090 as needed to operate the device in communication with an electronic device 1090.

FIG. 10C is a side view of the injection device 1000 in use. During use, the user grasps the injection device 1000 and presses on the spring-loaded button 1020 which ejects fluid from within a capsule 1028 of the injection device 1000 into the tissue at an insertion area 30 of the recipient.

Figure 11A:
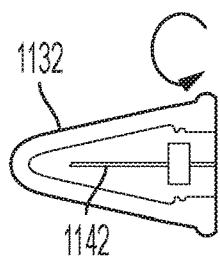
FIGS. 11A-D illustrate another injection device with an injection device tip (FIG. 11A), an interior view of the injection device (FIG. 11B); a top view of the injection device (FIG. 11C); and a view of instructions displayed on a screen of an electronic device (FIG. 11D)
Figure 11B:
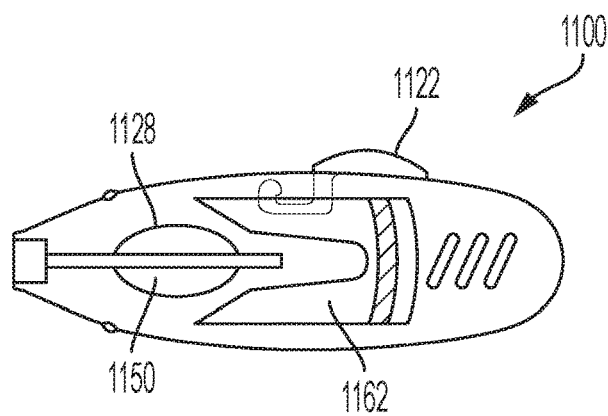

FIGS. 11A-D illustrate another injection device 1100 suitable for use with a fluid delivery assembly. FIG. 11A illustrates a cap 1132 with a needle 1142 for the injection device 1100. The cap 1132 with the needle 1142 are secured to the housing 1115 of the injection device to engage the needle 1142 with the fluid delivery assembly 1150. When the cap 1132 is removed, the needle 1142 remains engaged with the housing 1115. As shown in the interior view of the housing 1115 in FIG. 11B, a capsule 1128 contains the medicament. When the slider 1122 is advanced distally 20, the ejector 1162 engages the capsule 1128 and collapses the capsule 1128 to deliver the medicament through the needle 1142 to the patient.

Figure 11C:
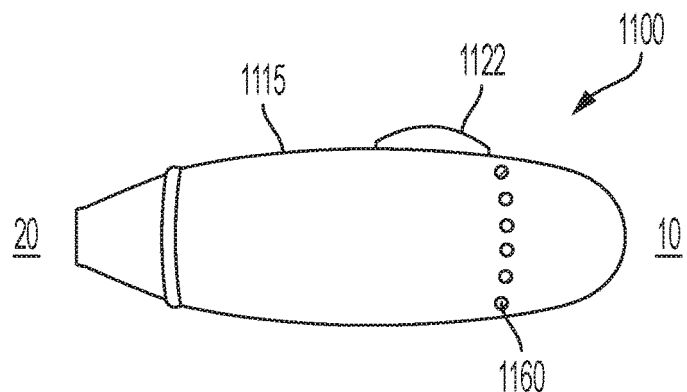
Figure 11D:
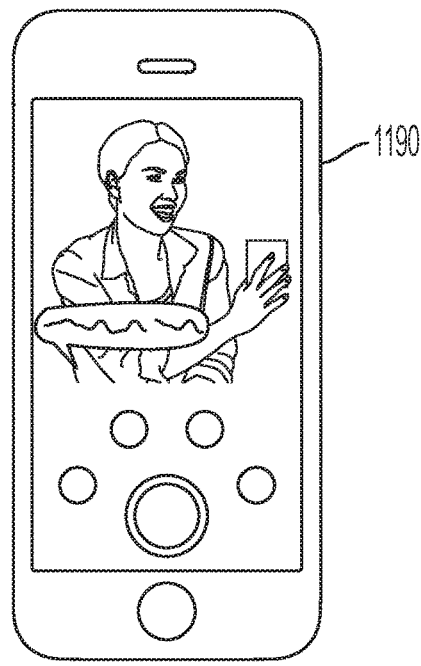

A visual indicator, such as a ring 1160 can be provided as shown in FIG. 11C. The ring 1160 changes color when the medication is delivered. The injection device 1100 is further configurable to include electronics to communicate with an electronic device 1190. As described above, the injection device can include suitable electronics, power supply, and memory components to operate the device.

FIGS. 12A-B illustrate a kit (FIG. 12A) and a perspective view of an injection device (FIG. 12B). The injection device 1200 is suitable for use with a fluid delivery assembly and can be provided as part of a kit 1201 in a package 1202 as shown in FIG. 12A. The package 1202 can be a rectangular box (as illustrated) with a lid 1204 that opens to reveal the injection device 1200. The lid 1204 can have a surface image 1206 as shown in FIG. 12A. The surface image 1206 can provide useful information for instructing a user on use during deployment. For medicaments that need to be administered on a schedule, an insert 1212 can also be provided which includes, for example, calendar stickers for use to keep track of when the medication is delivered.

As illustrated, the housing 1215 has a cap 1230. Two arms 1220, 1222 are provided. A reservoir or fluid delivery assembly fits between the two arms. When the user squeezes the two arms together the capsule 1228, such as those described above, is compressed and the medicament is delivered through the needle 1242 into the tissue 30. The two arms 1220, 1222 can further be configured to have ribs 1232 on an exterior facing surface which improve the user's grip during use. The fluid delivery assembly 1250 is shown positioned within the injection device 1200.

Figure 13A:
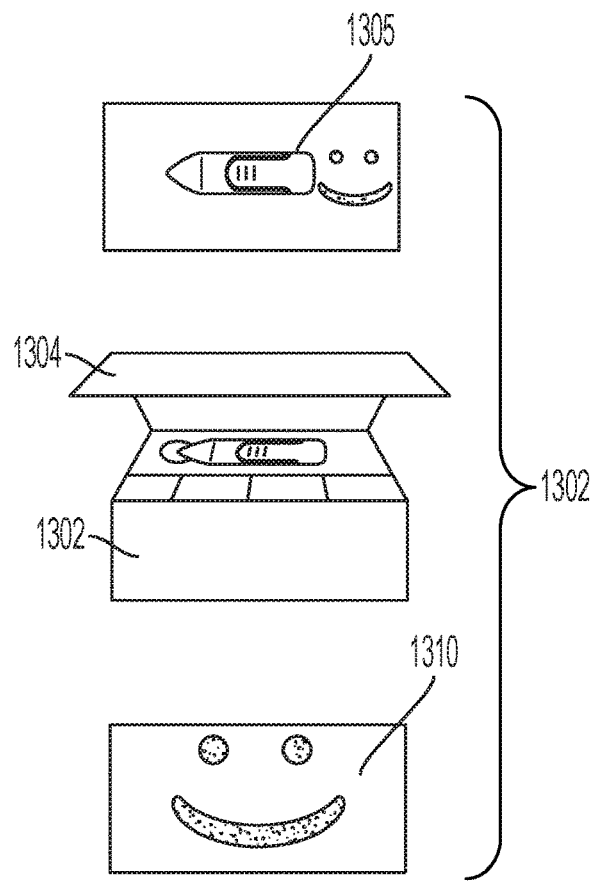
FIGS. 13A-D illustrate another exemplar injection device and system.

FIGS. 13A-D illustrate another exemplar injection device suitable for use with a fluid delivery assembly and system. This system is similar to the injection device shown in FIG. 12. FIG. 13A is a view of the packaging. The injection device 1300 is provided as part of a kit in a package 1302 as shown in FIG. 13A. The package 1302 can be a rectangular box (as illustrated) with a lid 1304 that opens to reveal the injection device 1300. The lid 1304 can have a surface image 1305 as shown in FIG. 13A. The surface image 1305 can be useful in instructing a user on use during deployment. For medicaments that need to be administered on a schedule, an insert 1310 can be provided. As discussed above, suitable electronics, power supply, and memory components can be included to operate the device.

Figure 13B:
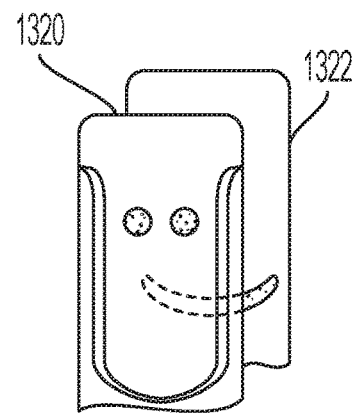

FIG. 13B is a perspective view of a proximal portion of the injection device 1300. Two arms 1320, 1322 are provided. When the two arms 1320, 1322 are pressed together, an image like the one shown in the insert 1310 can be seen by the user to let the user know that enough force is applied to achieve full expulsion of the medicament.

Figure 13C:
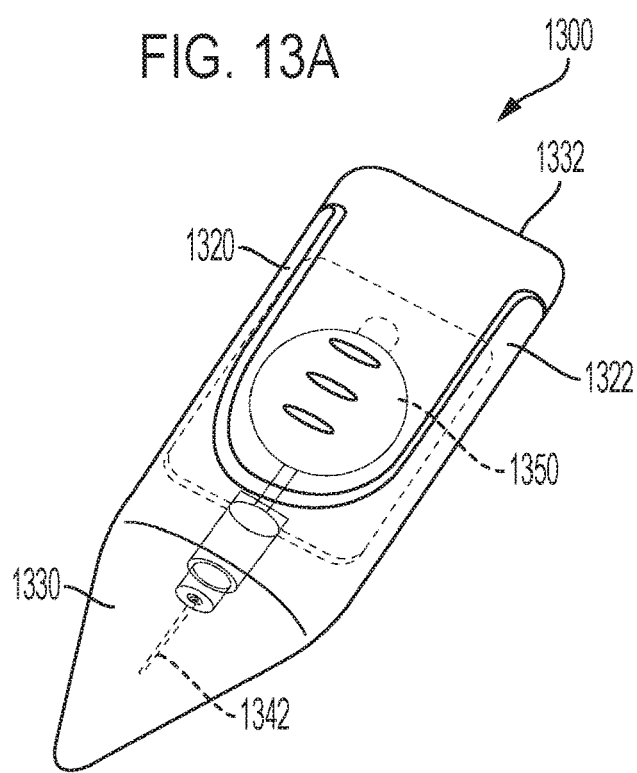

FIG. 13C is a perspective view of an injection device 1300 having a housing. A sliding sleeve 1330 can be provided which slides to reveal the needle 1342. The fluid delivery assembly 1350 is shown positioned within the injection device 1300.

Figure 13D:
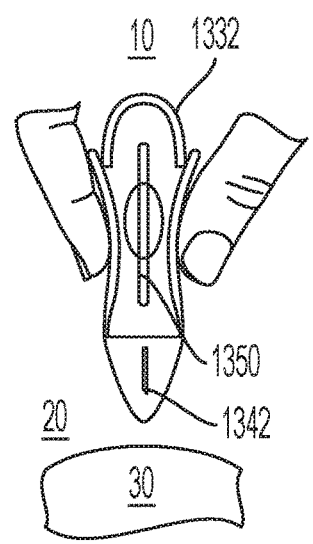

FIG. 13D is a side view of the injection device in use. When the user squeezes the two arms 1320, 1322 together the capsule of the fluid delivery assembly 1350 is compressed and the medicament is delivered through the needle 1342 into the tissue 30. A curved insert 1332 is provided which provides additional mechanical leverage to compress the capsule 1328 of the fluid delivery assembly 1350. The overall construction of the outer shell provides additional leverage. An opening is provided that allows the sliding sleeve 1330 to move backwards and forwards along an axis.

FIGS. 14A-C illustrate another exemplar injection device 1400 suitable for use with a fluid delivery assembly and system. FIG. 14A is a view of the packaging. The package 1402 can be a rectangular box (as illustrated) with a lid 1404 that opens to reveal the injection device 1400. The lid 1404 can have a surface image 1405.

FIG. 14B is a perspective view of the injection device 1400 which is in communication with an electronic device 1490. The injection device 1400 has a spherical shape and a pop-up timer 1410. The electronic device 1490 includes a power supply, and memory components to operate the device. The fluid delivery assembly 1450 is shown positioned within an interior of the housing of the injection device 1400.

FIG. 14C is a side view of the injection device in use. When the user squeezes the spherical shaped housing 1415, the capsule 1428 is compressed and the medicament is delivered through the needle 1442 into the tissue 30 of the patient.

Figure 15A:
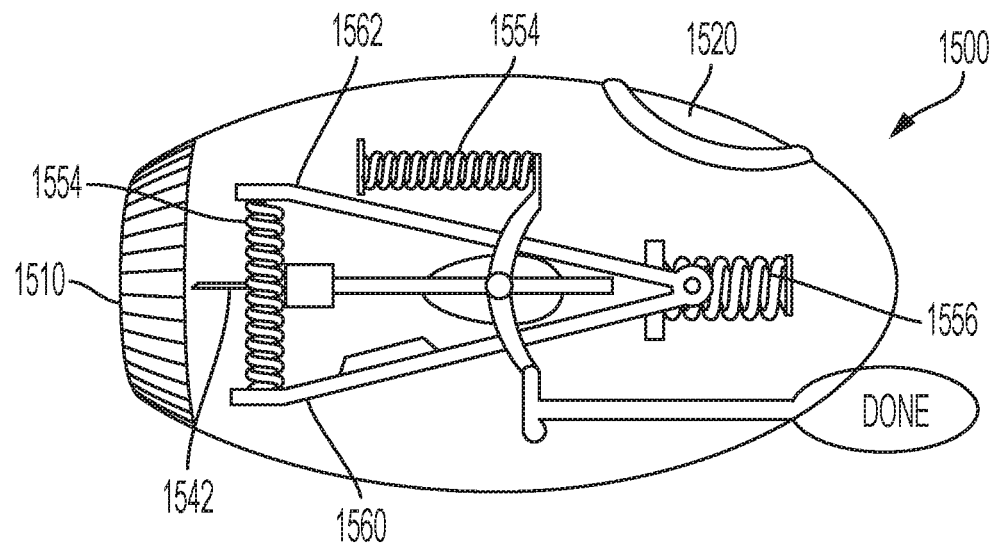
FIGS. 15A-B illustrate an interior view (FIG. 15A) and exterior view (FIG. 15B) of an ovoid injection device.
Figure 15B:
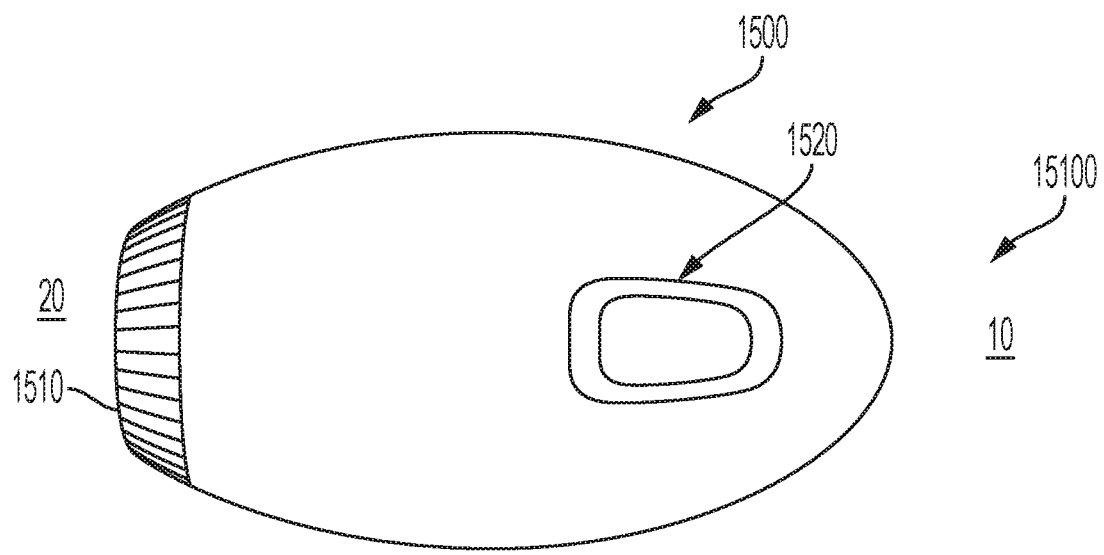

FIGS. 15A-B illustrate an interior view (FIG. 15A) and exterior view (FIG. 15B) of an ovoid injection device 1500 suitable for use with a fluid delivery assembly. The ovoid injection device has a twist off cap 1510. Once the button 1520 is pressed, the mechanism shown in FIG. 15A is activated. A first spring 1556 advances the needle 1542 in a distal direction. Once the needle 1542 penetrates the skin of the patient, the user presses the levers 1561, 1562 towards each other to squeeze the drug holding reservoir causing the drug to be ejected into the patient. Once the levers 1561, 1562 are fully pressed towards each other, a second spring 1554 is activated. Activation of the second spring 1554 pulls the entire assembly in a proximal direction and withdraws the needle 1542 from the tissue. An indicator can be provided which becomes visible to let the user or patient know the injection is complete ("DONE").

FIGS. 16A-D illustrate another exemplar injection device 1600 suitable for use with a fluid delivery assembly and system. FIG. 16A is a view of the packaging. The package 1602 can be a rectangular box (as illustrated) with a lid 1604 that opens to reveal the injection device 1600. The lid 1604 can have a surface image 1605. FIG. 16B is a side view of the injection device with a housing 1615 and a cap 1630.

FIG. 16C illustrates the injection device 1600 in wireless communication with an electronic device 1690, such as a cell phone, which in turn is in communication with a central location such as a database housed in the cloud 1695. The injection device 1600 has an ovoid shape with a cap. The cap can be frosted and removable. The fluid delivery assembly 1650 is shown positioned within the injection device 1600.

FIG. 16D is a side view of the injection device 1600 in use. When the user squeezes the housing 1615, the capsule of the fluid delivery assembly 1650 is compressed and the medicament is delivered through the needle 1642 into the tissue 30.

Figure 17A:
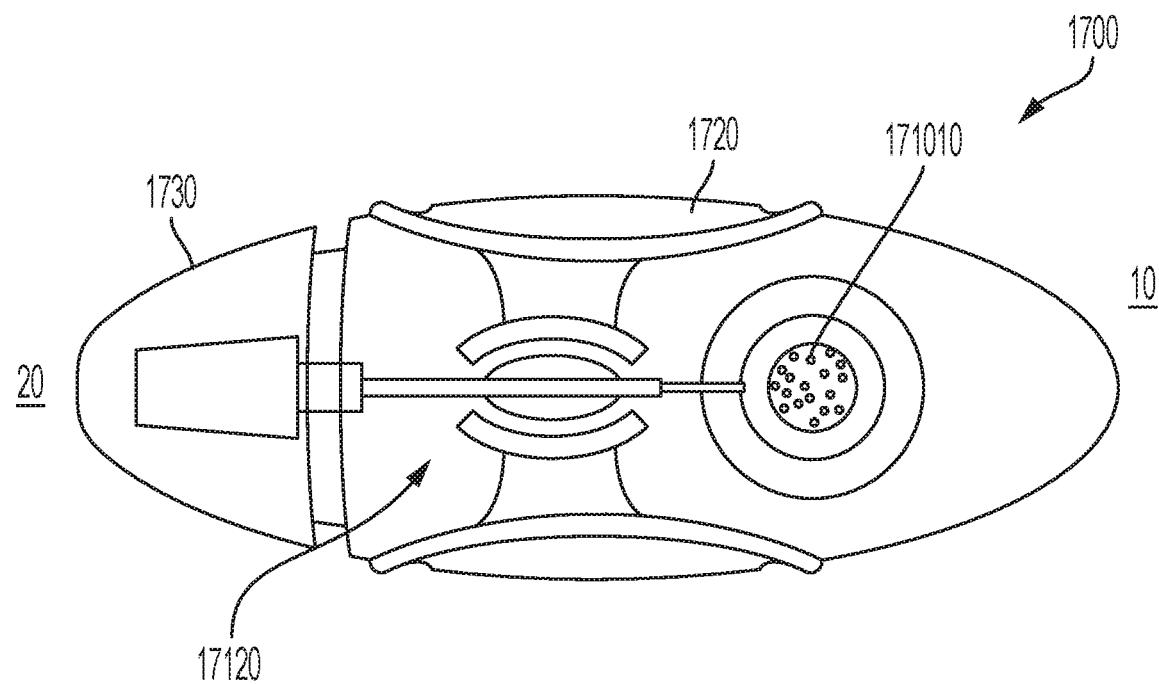
FIGS. 17A-B illustrate an interior view (FIG. 17A) and exterior view (FIG. 17B) of an injection device.
Figure 17B:
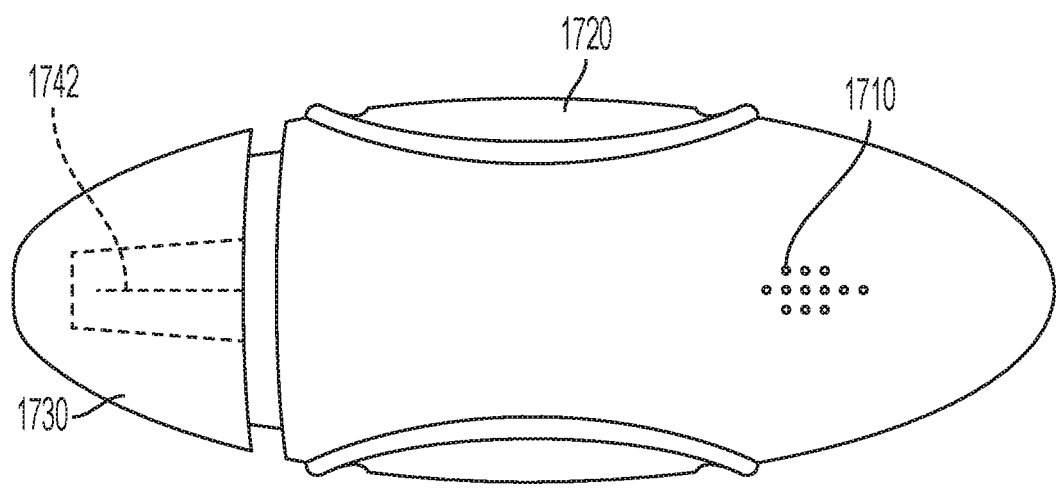

FIGS. 17A-B illustrate an interior view (FIG. 17A) and exterior view (FIG. 17B) of an exemplar injection device 1700 suitable for use with a fluid delivery assembly. A film strip sensor can be provided which senses pressure on the housing 1715. A speaker 1710 can be provided which provides instructions to the user during use. Suitable electronics, power supply, and memory components may be included as needed to operate the speaker. A button 1720 is provided for the user to engage and a cap 1730 is provided at the distal end 20 to enclose the needle 1742.

FIGS. 18A-C illustrate another exemplar injection device 1800 suitable for use with a fluid delivery assembly and system 1805. FIG. 18A is a view of the packaging 1802 with a lid 1801. FIG. 18B is a perspective view of the injection device 1800 which is in communication with an electronic device 1890 as part of a system 1805. The fluid delivery assembly 1850 is shown positioned within the housing of the injection device 1800. FIG. 18C is a side view of the injection device in use. An LED indicator guide 1810 can be provided. As with other embodiments, suitable electronics, power supply, and memory components can be included, as needed, to operate the device.

During preparation for use, the user removes the injection device of any of the embodiments described above from the packaging. As noted above, the user can be a healthcare practitioner or the patient.

As desirable, the injection device is shaken to ensure that the medicaments are mixed as noted in FIG. 4. The user can inspect the appearance of the medicaments to confirm the appearance of the medicament and lack of contaminants. Any needle cover or guard is removed, and the user then applies the tip of the device to a surface of the patient where the medicament is to be injected. Once placed, the user presses the delivery button to deliver the medicament to the patient.

As will be appreciated by those skilled in the art, a variety of materials can be used to make the devices disclosed herein. For example, rigid parts (such as the body cap, the body and the lock) can be made from injection moldable plastics such as but not limited to: ABS, Acrylic, Nylon, Polycarbonbate, Polystyrene, etc. The needle guard, for example needle guard 130, can be made from an elastomeric polymer such as but not limited to: Silicone, ethylene-vinyl-acetate (EVA), nitrile rubber, butyl rubber, etc.

Any of the disclosed injection devices can be configurable to include one or more of the following features:

- Electronics to provide for communication between the injection device and an electronic device or a central location (such as a doctor's office)
- Electronics to provide sound or light
- Power supply
- Slogans, graphic instructions and/or visual images on the packaging to facilitate use of the injection device
- Luxury feel packaging
- Needle free training device
- Dose timer (for example, provided on the injection device case, on the injection device or provided via an electronic device)
- One or more tabs to facilitate removing a sterile barrier, e.g., by gripping the tab and peeling apart
- Automated needle/septum piercing process
- Flip down shield
- Snap-off cap
- Color ring on needle sleeve to indicate proper needle depth
- Lights which are activated when the injection device is pressed securely in place
- Audible coaching during injection process or for stress management by the injection device or via an electronic device
- Depth window in the housing
- Hidden needle prior to injection
- One or more springs, for example to deliver force to a medication reservoir to deliver medication to the patient
- Plunger color change indicator
- Speaker for issuing an audible beep when needle is uncapped
- Temperature indicator
- LEDs for visibility
- Optical sensor
- Contact sensor in needle cap The disclosed injection devices may also be configurable to communicate with an electronic device. The disclosed devices may also be configurable to communication with a remote server either via an electronic device or directly. Software may be used to provide instructions and/or notifications to a user.

The following is a disclosure by way of example of a suitable computing device (e.g., electronic device) which may be used with the presently disclosed injection devices. The description of the various components of a computing device is not intended to represent any particular architecture or manner of interconnecting the components. Other systems that have fewer or more components may also be used with the disclosed subject matter. A communication device may constitute a form of a computing device and may at least include, contain, utilize or emulate a computing device. The computing device may include an interconnect (e.g., bus and system core logic), which can interconnect such components of a computing device to a data processing device, such as a processor(s) or a microprocessor(s) or a controller(s), or other form of partly or completely programmable or pre-programmed device, e.g., hard wired and/or application specific integrated circuit ("ASIC") customized logic circuitry, such as may implement, e.g., a controller or microcontroller, a digital signal processor, or any other form of device that can fetch and perform instructions, operate on pre-loaded/pre-programmed instructions, and/or follow instructions found in hard-wired or customized circuitry, such as above noted forms of hard-wired circuitry containing logic circuitry, in order to carry out logic operations that, together, perform steps of and whole processes and functionalities as described in the present disclosure.

In this description, various functions, functionalities and/or operations may be described as being performed by or caused by software program code to simplify the description. However, those skilled in the art will recognize that what is meant by such expressions is that the functions resulting from execution of the program code/instructions are performed by a computing device as described in the present application, e.g., including a processor, such as a microprocessor, microcontroller, logic circuit or the like noted above. Alternatively, or in combination, the functions and operations can be implemented using special purpose circuitry, with or without software instructions, such as using an Application-Specific Integrated Circuit(s) (ASIC) or a Field-Programmable Gate Array(s) (FPGA), which may be programmable, partly programmable or hard wired.

Embodiments can thus be implemented using hard wired circuitry without program software code/instructions, or in combination with circuitry using programmed software code/instructions.

Thus, the techniques are limited neither to any specific combination of hardware circuitry and software, nor to any particular tangible source for the instructions executed by the data processor(s) within the computing device, such as a tangible machine readable medium. In other words, as an example only, part or all of the machine readable medium may in part or in full form a part of the, or be included within the computing device itself, e.g., as the above noted hard wiring or pre-programmed instructions in any memory utilized by or in the computing device.

While some embodiments of systems incorporating the disclosed injection devices can be implemented in fully functioning computers and computer systems, various embodiments are capable of being distributed as a computing device including, e.g., a variety of architecture(s), form (s) or component(s). Embodiments may be capable of being applied regardless of the particular type of machine or tangible machine/computer readable media used to actually affect the performance of the functions and operations and/or the distribution of the performance of the functions, functionalities and/or operations.

The interconnect may connect the data processing device to defined logic circuitry including, e.g., a memory. The interconnect may be internal to the data processing device, such as coupling a microprocessor to on-board cache memory, or external (to the microprocessor) memory such as main memory, or a disk drive, or external to the computing device, such as a remote memory, a disc farm or other mass storage device(s), etc.

The inter-connect in addition to interconnecting such as microprocessor(s) and memory may also interconnect such elements to a display controller and/or display device, and/or to other peripheral devices. The interconnect may include one or more buses connected to one another through various forms of a bridge(s), a controller(s) and/or an adapter(s). In one embodiment an I/O controller may include a USB (Universal Serial Bus) adapter for controlling a USB peripheral(s), and/or an IEEE-1394 bus adapter for controlling an IEEE-1394 peripheral(s).

The storage device, i.e., memory may include any tangible machine readable media, which may include but are not limited to recordable and non-recordable type media such as a volatile or non-volatile memory device(s), such as volatile RAM (Random Access Memory), typically implemented as a dynamic RAM (DRAM) which requires power continually in order to refresh or maintain the data in the memory, and a non-volatile ROM (Read Only Memory), and other types of non-volatile memory, such as a hard drive, flash memory, detachable memory stick, etc. Non-volatile memory typically may include a magnetic hard drive, a magnetic/optical drive, or an optical drive (e.g., a DVD RAM, a CD ROM, a DVD or a CD), or other type of memory system which maintains data even after power is removed from the system.

Where the disclosed device communicates with a central location, a server could be made up of one or more computing devices. A server can be utilized, e.g., in a network to host a network database, compute necessary variables and information from information in the database(s), store and recover information from the database(s), track information and variables, provide interfaces for uploading and downloading information and variables, and/or sort or otherwise manipulate information and data from the database(s). In one embodiment a server can be used in conjunction with another computing device(s) positioned locally or remotely to execute instructions, e.g., to perform certain algorithms, calculations and other functions as may be included in the operation of the system(s) and method(s) of the disclosed subject matter, as disclosed in the present application.

At least some aspects of the disclosed subject matter can be embodied, at least in part, in programmed software code/instructions. That is, the functions, functionalities and/ or operations and techniques may be carried out in a computing device or other data processing system in response to its processor, such as a microprocessor, executing sequences of instructions contained in a memory or memories, such as ROM, volatile RAM, non-volatile memory, cache or a remote storage device. In general, the routines executed to implement the embodiments of the disclosed subject matter may be implemented as part of an operating system or a specific application, component, program, object, module or sequence of instructions usually referred to as a "computer program(s)," or "software." The computer program(s) typically comprises instructions stored at various times in various tangible memory and storage devices, e.g., in a computing device, such as in cache memory, main memory, internal disk drives, and/or above noted forms of external memory, such as remote storage devices, such as a disc farm, remote memory or databases, e.g., accessed over a network, such as the Internet. When read and executed by a computing device, e.g., by a processor(s) in the computing device, the computer program causes the computing device to perform a method(s), e.g., process and operation steps to execute an element(s) as part of some aspect(s) of the system(s) or method(s) of the disclosed subject matter.

A tangible machine-readable medium can be used to store software and data that, when executed by a computing device, causes the computing device to perform a method(s) as may be recited in one or more accompanying claims defining the disclosed subject matter. The tangible machine-readable medium may include storage of the executable software program code/instructions and data in various tangible locations as noted above. Further, the program software code/instructions can be obtained from remote storage, including, e.g., through centralized servers or peer to peer networks and the like. Different portions of the software program code/instructions and data can be obtained at different times and in different communication sessions or in a same communication session, e.g., with one or many storage locations.

The software program code/instructions and data can be obtained in their entirety prior to the execution of a respective software application by the computing device. Alternatively, portions of the software program code/instructions and data can be obtained dynamically, e.g., just in time, when needed for execution. Alternatively, some combination of these ways may be used for obtaining the software program code/instructions and data may occur, as an example, for different applications, components, programs, objects, modules, routines or other sequences of instructions or organization of sequences of instructions. Thus, it is not required that the data and instructions be on a single machine-readable medium in entirety at any particular instant of time or at any instant of time ever.

In general, a tangible machine readable medium can include any tangible mechanism that provides (i.e., stores) information in a form accessible by a machine (e.g., a computing device), which may be included, e.g., in a communication device, a network device, a personal digital assistant, a mobile communication device, whether or not able to download and run applications from the communication network, such as the Internet, e.g., an I-phone, Droid, or the like, a manufacturing tool, or any other device including a computing device, comprising, e.g., one or more data processors, etc. In an embodiment(s), a user terminal can be a computing device, such as in the form of or included within a PDA, a cellular phone, a notebook computer, a personal desktop computer, etc. Alternatively, any traditional communication client(s) may be used in some embodiments of the disclosed subject matter. While some embodiments of the disclosed subject matter have been described in the context of fully functioning computing devices and computing systems, those skilled in the art will appreciate that various embodiments of the disclosed subject matter are capable of being distributed, e.g., as a system, method and/or software program product in a variety of forms and are capable of being applied regardless of the particular type of computing device machine or machine readable media used to actually effect the distribution.

The disclosed subject matter may be described with reference to block diagrams and operational illustrations or methods and devices to provide the system(s) and/or method (s) according to the disclosed subject matter. It will be understood that each block of a block diagram or other operational illustration (herein collectively, "block diagram"), and combination of blocks in a block diagram, can be implemented by means of analog or digital hardware and computer program instructions. These computing device software program code/instructions can be provided to the computing device such that the instructions, when executed by the computing device, e.g., on a processor within the computing device or other data processing apparatus, the program software code/instructions cause the computing device to perform functions, functionalities and operations of the system(s) and/or method(s) according to the disclosed subject matter, as recited in the accompanying claims, with such functions, functionalities and operations specified in the block diagram.

It will be understood that in some possible alternate implementations, the function, functionalities and operations noted in the blocks of a block diagram may occur out of the order noted in the block diagram. For example, the function noted in two blocks shown in succession can in fact be executed substantially concurrently or the functions noted in blocks can sometimes be executed in the reverse order, depending upon the function, functionalities and operations involved. Therefore, the embodiments of the system(s) and/or method(s) presented and described as a flowchart(s) in the form of a block diagram in the present application are provided by way of example only, and in order to provide a more complete understanding of the disclosed subject matter. The disclosed flow and concomitantly the method(s) performed as recited in the accompanying claims are not limited to the functions, functionalities and operations illustrated in the block diagram(s) and/or logical flow(s) presented in the disclosed subject matter. Alternative embodiments are contemplated in which the order of the various functions, functionalities and operations may be altered and in which sub-operations described as being part of a larger operation may be performed independently or performed differently than illustrated or not performed at all.

Although some of the drawings may illustrate a number of operations in a particular order, functions, functionalities and/or operations which are not now known to be order dependent, or become understood to not be order dependent, may be reordered. Other functions, functionalities and/or operations may be combined or broken out. While some reordering or other groupings may have been specifically mentioned in the present application, others will be or may become apparent to those of ordinary skill in the art and so the disclosed subject matter does not present an exhaustive list of alternatives. It should also be recognized that the aspects of the disclosed subject matter may be implemented in parallel or seriatim in hardware, firmware, software or any combination(s) of these, co-located or remotely located, at least in part, from each other, e.g., in arrays or networks of computing devices, over interconnected networks, including the Internet, and the like.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the claims presented define the scope of the invention and that methods and structures within the scope of these claims and their equivalents be covered thereby.

What is claimed is:

1. An injection device for delivery a liquid medicament comprising:
    a housing having a first end, a second end and an exterior surface wherein the housing defines a recess;
    a cap engaging a first end of the housing;
    a press-point positioned on the exterior surface of the housing wherein the press-point has a first location and a second location;
    a needle in communication with a drug reservoir and extending from the second end of the housing;
    a needle cover;
    a needle guard having a first cross-sectional area at a proximal end and a second cross-sectional area at a distal end, wherein the first cross-sectional area is larger than the second cross-sectional area, wherein the needle guard engages the second end of the housing and surrounds at least a portion of the needle cover;
    a needle shield extending from the second end of the housing positioned within the needle guard;
    the drug reservoir positionable within the recess of the housing, wherein the drug reservoir comprises a fluid capsule in fluid communication with a first tubular member, the needle positioned within a second tubular member in fluid communication with the first tubular member.

2. The injection device of claim 1, wherein the needle cover is removable.

3. The injection device of claim 1, further comprising a hinged panel on the exterior surface of the housing.

4. The injection device of claim 1, wherein the cap has a breakable seal.

5. The injection device of claim 1, wherein the needle guard is collapsible.

6. The injection device of claim 1, wherein the drug reservoir is accessible via an aperture on the exterior surface of the housing.

7. The injection device of claim 1 wherein the fluid medicament is a vaccine or an active agent.

8. The injection device of claim 7 wherein the active agent is a hormone used for the treatment of menopausal troubles or for contraception.

9. The injection device of claim 1 wherein the press-point further comprises a live hinge.

10. The injection device of claim 1 further comprising a communicator configured to wirelessly communicate with a second device.

11. A method of using an injection device to administer a liquid medicament comprising:
- providing an injection device comprising a housing having a first end, a second end and an exterior surface wherein the housing defines a recess, a cap engaging a first end of the housing, a press-point positioned on the exterior surface of the housing wherein the press-point has a first location and a second location, a needle in communication with a drug reservoir and extending from the second end of the housing, a needle cover, a needle guard having a first cross-sectional area at a proximal end and a second cross-sectional area at a distal end, wherein the first cross-sectional area is larger than the second cross-sectional area, wherein the needle guard engages the second end of the housing and surrounds at least a portion of the needle cover, and a needle shield extending from the second end of the housing positioned within the needle guard, the drug reservoir positionable within the recess of the 14 housing, wherein the drug reservoir comprises a fluid capsule in fluid communication 15 with a first tubular member, the needle positioned within a second tubular member in fluid communication with the first tubular member;
- pushing the cap in a distal direction to drive a proximal end of the needle through a seal;
- placing a distal end of the injection device adjacent a delivery surface; and applying pressure to the press-point.

12. The method of claim 11 wherein the method further comprises ones or more steps of removing the needle cover and twisting the cap of the injection device to break a seal.

13. The method of claim 11 wherein the press point of the injection device further comprises a live hinge wherein the method further comprises the step of applying pressure to the live hinge to achieve an audible click.

14. The method of claim 11 wherein the fluid medicament is a vaccine or an active agent.

15. The method of claim 14 wherein the active agent is a hormone used for the treatment of menopausal troubles or for contraception.

16. A kit comprising:
- a container; and
- an injection device comprising a housing having a first end, a second end and an exterior surface wherein the housing defines a recess, a cap engaging a first end of the housing, a press-point positioned on the exterior surface of the housing wherein the press-point has a first location and a second location, a needle in communication with a drug reservoir and extending from the second end of the housing, a needle cover, a needle guard having a first cross-sectional area at a proximal end and a second cross-sectional area at a distal end, wherein the first cross-sectional area is larger than the second cross-sectional area, wherein the needle guard engages the second end of the housing and surrounds at least a portion of the needle cover, wherein the drug reservoir is positionable within the recess of the housing, wherein the drug reservoir comprises a fluid capsule in fluid communication with a first tubular member, the needle positioned within a second tubular member in fluid communication with the first tubular member.

17. The kit of claim 16 further comprising one or more of instructions, and a calendar.

18. A system for communicating information comprising:
- an injection device comprising a housing having a first end, a second end and an exterior surface wherein the housing defines a recess, a cap engaging a first end of the housing, a press-point positioned on the exterior surface of the housing wherein the press-point has a first location and a second location, a needle in communication with a drug reservoir and extending from the second end of the housing, a needle cover, a needle guard having a first cross-sectional area at a proximal end and a second cross-sectional area at a distal end, wherein the first cross-sectional area is larger than the second cross-sectional area, wherein the needle guard engages the second end of the housing and surrounds at least a portion of the needle cover, and a needle shield extending from the second end of the housing positioned within the needle guard, the drug reservoir positionable within the recess of the housing, wherein the drug reservoir comprises a fluid capsule in fluid communication with a first tubular member, the needle positioned within a second tubular member in fluid communication with the first tubular member, and one or more of a communicator, a controller, a memory and a power supply; and
- an electronic device in wireless communication with the injection device.

19. The system for communicating information of claim 18 wherein the injection device is in communication with a central location via the electronic device.

20. The system for communicating information of claim 19 wherein the system is further configured to communicate information from the central location to at least one of the electronic device and the injection device.

21. The system for communicating information of claim 19 wherein the system is further configured to communicate information from at least one of the electronic device and the injection device to the central location.

* * * * *